US011351330B2

(12) United States Patent
Leonard et al.

(10) Patent No.: US 11,351,330 B2
(45) Date of Patent: Jun. 7, 2022

(54) SYSTEMS AND METHODS FOR HIGH VELOCITY NASAL INSUFFLATION

(71) Applicant: Vapotherm, Inc., Exeter, NH (US)

(72) Inventors: Scott A. Leonard, Bedford, NH (US); Brian Green, Westford, MA (US); John Allen, North Andover, MA (US); David Adams, North Hampton, NH (US); Marc Gervais, Weare, NH (US); Mark Kolnsberg, Beverly, MA (US); Richelle Helman, Kingston, NH (US)

(73) Assignee: Vapotherm, Inc., Exeter, NH (US)

( * ) Notice: Subject to any disclaimer, the term of this patent is extended or adjusted under 35 U.S.C. 154(b) by 196 days.

(21) Appl. No.: 15/783,566

(22) Filed: Oct. 13, 2017

(65) Prior Publication Data
US 2018/0104436 A1 Apr. 19, 2018

Related U.S. Application Data

(60) Provisional application No. 62/408,560, filed on Oct. 14, 2016.

(51) Int. Cl.
*A61M 16/14* (2006.01)
*A61M 16/16* (2006.01)
(Continued)

(52) U.S. Cl.
CPC ...... *A61M 16/142* (2014.02); *A61M 16/0066* (2013.01); *A61M 16/0096* (2013.01);
(Continued)

(58) Field of Classification Search
CPC ................ A61M 16/142; A61M 16/14; A61M 16/0672; A61M 16/101; A61M 16/0066;
(Continued)

(56) References Cited

U.S. PATENT DOCUMENTS 2,742,040 A 4/1956 Moore et al.
3,659,604 A 5/1972 Melville et al.
(Continued)

FOREIGN PATENT DOCUMENTS

CA 2622734 A1 6/2007
DE 2843756 A1 4/1980
(Continued)

OTHER PUBLICATIONS

International Search Report and Written Opinion for International Application No. PCT/US2007/021469 dated Oct. 13, 2008.
(Continued)

*Primary Examiner* — Elliot S Ruddie
(74) *Attorney, Agent, or Firm* — White & Case LLP

(57) ABSTRACT

Systems, methods, and devices for humidifying a breathing gas are presented. The system includes a base unit, a vapor transfer unit, a nasal cannula, and a liquid container. The base unit includes a blower. The vapor transfer unit is external to the base unit and includes a gas passage, a liquid passage, a gas outlet, and a membrane separating the gas passage and the liquid passage. The membrane permits transfer of vapor into the gas passage from liquid in the liquid passage. The nasal cannula is coupled to the gas outlet. The liquid container is configured to reversibly mate with the base unit.

22 Claims, 14 Drawing Sheets

(51) Int. Cl.
*A61M 16/06* (2006.01)
*A61M 16/10* (2006.01)
*A61M 16/00* (2006.01)
*A61M 16/20* (2006.01)

(52) U.S. Cl.
CPC ...... *A61M 16/0672* (2014.02); *A61M 16/101* (2014.02); *A61M 16/16* (2013.01); *A61M 16/162* (2013.01); *A61M 16/20* (2013.01); *A61M 16/0069* (2014.02); *A61M 16/0666* (2013.01); *A61M 16/201* (2014.02); *A61M 2016/003* (2013.01); *A61M 2016/0027* (2013.01); *A61M 2016/1025* (2013.01); *A61M 2202/0208* (2013.01); *A61M 2205/0272* (2013.01)

(58) Field of Classification Search
CPC .............. A61M 16/0096; A61M 16/16; A61M 16/162; A61M 16/20; A61M 16/1045; A61M 2016/0027; A61M 2016/102; A61M 2016/1025; A61M 2202/0208; A61M 2205/0272; A61M 2205/3379; A61M 2205/3386; A61M 2205/3389; A61M 2205/3393; F24F 6/00; F24F 6/02–043; F24F 2006/008; F24F 2006/046; F24F 6/08–10; F24F 6/16–18
USPC ............ 126/113; 137/403; 177/211; 392/402
See application file for complete search history.

(56) References Cited

U.S. PATENT DOCUMENTS

| | | | |
|---|---|---|---|
| 3,744,771 A * | 7/1973 | Deaton | A61M 16/16 |
| | | | 261/78.2 |
| 3,871,373 A | 3/1975 | Jackson | |
| 3,903,216 A | 9/1975 | Allan et al. | |
| 3,923,057 A | 12/1975 | Chalon | |
| 4,010,748 A | 3/1977 | Dobritz | |
| 4,013,742 A | 3/1977 | Lang | |
| 4,028,444 A | 6/1977 | Brown et al. | |
| 4,028,445 A | 6/1977 | Hickmann et al. | |
| 4,036,919 A | 7/1977 | Komendowski et al. | |
| 4,051,205 A | 9/1977 | Grant | |
| 4,098,853 A | 7/1978 | Brown et al. | |
| 4,110,419 A | 8/1978 | Miller | |
| 4,163,371 A | 8/1979 | Groninger | |
| 4,172,105 A | 10/1979 | Miller et al. | |
| 4,319,566 A | 3/1982 | Hayward et al. | |
| 4,354,984 A | 10/1982 | Richardson et al. | |
| 4,366,105 A | 12/1982 | Nowacki | |
| 4,369,777 A | 1/1983 | Lwoff et al. | |
| 4,381,267 A | 4/1983 | Jackson | |
| 4,430,994 A | 2/1984 | Clawson et al. | |
| 4,463,755 A | 8/1984 | Suzuki | |
| 4,500,480 A | 2/1985 | Cambio, Jr. | |
| 4,532,088 A | 7/1985 | Miller | |
| 4,589,409 A | 5/1986 | Chatburn et al. | |
| 4,621,633 A | 11/1986 | Bowles et al. | |
| 4,632,677 A | 12/1986 | Blackmer | |
| 4,644,790 A | 2/1987 | Mizoguchi | |
| 4,648,395 A | 3/1987 | Sato et al. | |
| 4,652,408 A | 3/1987 | Montgomery | |
| 4,657,713 A | 4/1987 | Miller | |
| 4,682,010 A | 7/1987 | Drapeau et al. | |
| 4,753,758 A | 6/1988 | Miller | |
| 4,765,327 A | 8/1988 | Shim | |
| 4,810,854 A | 3/1989 | Jursich et al. | |
| 4,838,258 A | 6/1989 | Dryden et al. | |
| 4,910,384 A | 3/1990 | Silver | |
| 4,921,642 A | 5/1990 | LaTorraca | |
| 4,941,469 A | 7/1990 | Adahan | |
| 4,943,704 A | 7/1990 | Rabenau et al. | |
| 4,955,372 A | 9/1990 | Blackmer et al. | |
| 4,957,107 A | 9/1990 | Sipin | |
| 4,973,231 A | 11/1990 | Colliver | |
| 5,031,612 A | 7/1991 | Clementi | |
| 5,036,847 A | 8/1991 | Boussignac et al. | |
| 5,038,840 A | 8/1991 | Fair | |
| 5,065,756 A | 11/1991 | Rapoport | |
| 5,255,674 A | 10/1993 | Oftedal et al. | |
| 5,329,939 A | 7/1994 | Howe | |
| 5,336,156 A | 8/1994 | Miller et al. | |
| 5,349,946 A | 9/1994 | McComb | |
| 5,367,604 A | 11/1994 | Murray | |
| 5,392,770 A | 2/1995 | Clawson et al. | |
| 5,431,885 A | 7/1995 | Zlotnik et al. | |
| 5,437,634 A | 8/1995 | Amano | |
| 5,445,143 A | 8/1995 | Sims | |
| 5,454,368 A | 10/1995 | Tarulli | |
| 5,474,062 A | 12/1995 | DeVires et al. | |
| 5,529,060 A | 6/1996 | Salmon et al. | |
| 5,558,084 A | 9/1996 | Daniell et al. | |
| 5,572,992 A | 11/1996 | Kankkunen et al. | |
| 5,577,494 A | 11/1996 | Kuypers et al. | |
| 5,588,423 A | 12/1996 | Smith | |
| 5,623,922 A | 4/1997 | Smith | |
| 5,724,957 A | 3/1998 | Rubsamen et al. | |
| 5,752,498 A * | 5/1998 | Lake | F24F 6/02 |
| | | | 126/113 |
| 5,769,071 A | 6/1998 | Turnbull | |
| 5,823,184 A | 10/1998 | Gross | |
| 5,901,705 A | 5/1999 | Leagre | |
| 6,010,118 A | 1/2000 | Milewicz | |
| 6,041,777 A | 3/2000 | Faithfull et al. | |
| 6,050,260 A | 4/2000 | Daniell et al. | |
| 6,095,505 A | 8/2000 | Miller | |
| 6,102,037 A | 8/2000 | Koch | |
| 6,125,847 A | 10/2000 | Lin | |
| 6,129,082 A | 10/2000 | Leagre | |
| 6,142,971 A | 11/2000 | Daoud et al. | |
| 6,152,132 A | 11/2000 | Psaros | |
| 6,167,883 B1 | 1/2001 | Beran et al. | |
| 6,244,576 B1 | 6/2001 | Tsai | |
| 6,256,454 B1 | 7/2001 | Dykes | |
| 6,349,724 B1 | 2/2002 | Burton et al. | |
| 6,367,472 B1 | 4/2002 | Koch | |
| 6,397,841 B1 | 6/2002 | Kenyon et al. | |
| 6,410,465 B1 | 6/2002 | Lim et al. | |
| 6,454,997 B1 | 9/2002 | Divino, Jr. et al. | |
| 6,510,848 B1 | 1/2003 | Gibertoni | |
| 6,536,428 B1 | 3/2003 | Smith et al. | |
| 6,550,476 B1 | 4/2003 | Ryder | |
| 6,554,260 B1 | 4/2003 | Lipscombe et al. | |
| 6,560,408 B2 | 5/2003 | Glucksman et al. | |
| 6,613,280 B2 | 9/2003 | Myrick et al. | |
| 6,718,974 B1 | 4/2004 | Moberg | |
| 6,769,430 B1 | 8/2004 | Carlsen et al. | |
| 6,824,127 B2 | 11/2004 | Park et al. | |
| 6,827,046 B2 | 12/2004 | Welle | |
| 6,827,084 B2 | 12/2004 | Grubb, Jr. | |
| 6,904,911 B2 | 6/2005 | Gibertoni | |
| 6,912,977 B2 | 7/2005 | Cumming | |
| 6,918,389 B2 | 7/2005 | Seakins et al. | |
| 6,938,619 B1 | 9/2005 | Hickle | |
| 6,938,886 B2 | 9/2005 | Glucksman | |
| 6,953,354 B2 | 10/2005 | Edirisuriya et al. | |
| 6,988,497 B2 | 1/2006 | Levine | |
| 6,997,183 B2 | 2/2006 | Koch et al. | |
| 7,051,733 B2 | 5/2006 | Gradon et al. | |
| 7,066,452 B2 | 6/2006 | Rotering et al. | |
| 7,073,500 B2 | 7/2006 | Kates | |
| 7,077,135 B2 | 7/2006 | Pagan | |
| 7,080,645 B2 | 7/2006 | Genger et al. | |
| 7,081,560 B1 | 7/2006 | Lim et al. | |
| 7,086,399 B2 | 8/2006 | Makinson et al. | |
| 7,096,864 B1 | 8/2006 | Mayer et al. | |
| 7,106,955 B2 | 9/2006 | Thudor et al. | |
| 7,111,624 B2 | 9/2006 | Thudor et al. | |
| 7,137,388 B2 | 11/2006 | Virr et al. | |
| 7,140,367 B2 | 11/2006 | White et al. | |
| 7,146,979 B2 | 12/2006 | Seakins et al. | |
| 7,228,859 B2 | 6/2007 | Loescher | |

(56) References Cited

U.S. PATENT DOCUMENTS

| | | |
|---|---|---|
| 7,250,035 B1 | 7/2007 | Ott et al. |
| 7,306,205 B2 | 12/2007 | Huddart et al. |
| 7,314,046 B2 | 1/2008 | Schroeder et al. |
| 7,380,774 B2 | 6/2008 | Akita et al. |
| 7,428,902 B2 | 9/2008 | Du et al. |
| 7,493,902 B2 | 2/2009 | White et al. |
| 7,571,725 B2 | 8/2009 | Wickham et al. |
| 7,849,852 B2 | 12/2010 | Bremner et al. |
| 8,240,306 B2 | 8/2012 | Cortez, Jr. et al. |
| D671,206 S | 11/2012 | McGarrity et al. |
| 8,322,339 B2 | 12/2012 | Gottlib et al. |
| 8,333,195 B2 | 12/2012 | Cortez, Jr. et al. |
| 9,199,053 B1 | 12/2015 | Allum et al. |
| 2001/0050080 A1 | 12/2001 | Seakins et al. |
| 2001/0054422 A1 | 12/2001 | Smith et al. |
| 2001/0056258 A1 | 12/2001 | Evans |
| 2002/0000225 A1 | 1/2002 | Schuler et al. |
| 2002/0055685 A1 | 5/2002 | Levitsky et al. |
| 2002/0100320 A1 | 8/2002 | Smith et al. |
| 2002/0148471 A1 | 10/2002 | Hirabayashi |
| 2002/0195104 A1 | 12/2002 | Fini et al. |
| 2003/0098022 A1 | 5/2003 | Nakao et al. |
| 2003/0236015 A1 | 12/2003 | Edirisuriya et al. |
| 2004/0016432 A1 | 1/2004 | Genger et al. |
| 2004/0050386 A1 | 3/2004 | Levine |
| 2004/0234254 A1 | 11/2004 | Czupich et al. |
| 2005/0022828 A1 | 2/2005 | Fukunaga et al. |
| 2005/0166915 A1 | 8/2005 | Gibertoni |
| 2005/0169615 A1 | 8/2005 | Glucksman |
| 2005/0178383 A1 | 8/2005 | Mackie et al. |
| 2006/0021615 A1 | 2/2006 | Kertzman |
| 2006/0037613 A1 | 2/2006 | Kwok et al. |
| 2006/0113690 A1 | 6/2006 | Huddart et al. |
| 2006/0118111 A1 | 6/2006 | Pelerossi et al. |
| 2006/0130836 A1 | 6/2006 | Wixey et al. |
| 2006/0191531 A1 | 8/2006 | Mayer et al. |
| 2006/0213515 A1 | 9/2006 | Bremner et al. |
| 2006/0219243 A1 | 10/2006 | Walstrom |
| 2006/0243804 A1 | 11/2006 | Christoffersen et al. |
| 2006/0272639 A1 | 12/2006 | Makinson et al. |
| 2007/0137646 A1* | 6/2007 | Weinstein ............ A61M 16/16 128/204.17 |
| 2007/0175473 A1 | 8/2007 | Lewis et al. |
| 2007/0283958 A1 | 12/2007 | Naghavi |
| 2008/0072899 A1 | 3/2008 | Niland et al. |
| 2008/0078386 A1 | 4/2008 | Feldhahn et al. |
| 2008/0078393 A1 | 4/2008 | Acker et al. |
| 2008/0135044 A1 | 6/2008 | Freitag et al. |
| 2009/0056712 A1 | 3/2009 | Cortez, Jr. et al. |
| 2009/0090363 A1* | 4/2009 | Niland ............... A61M 16/026 128/203.26 |
| 2009/0165795 A1 | 7/2009 | Nadjafizadeh et al. |
| 2010/0059053 A1 | 3/2010 | Niland |
| 2010/0133292 A1 | 6/2010 | Ware et al. |
| 2010/0192957 A1 | 8/2010 | Hobson et al. |
| 2011/0144586 A1* | 6/2011 | Michaud ............ A61M 5/1413 604/151 |
| 2011/0214676 A1 | 9/2011 | Allum et al. |
| 2014/0174442 A1* | 6/2014 | Cortez, Jr. ........... A61M 16/08 128/203.26 |
| 2014/0311489 A1 | 10/2014 | Heine |
| 2015/0027204 A1 | 1/2015 | Stoks et al. |
| 2015/0048530 A1* | 2/2015 | Cheung ............... A61M 16/167 261/129 |
| 2015/0165142 A1 | 6/2015 | Tham et al. |
| 2015/0297877 A1* | 10/2015 | Pelkus .................. A61M 39/24 128/203.12 |
| 2016/0287832 A1* | 10/2016 | Cortez, Jr. ........ A61M 16/0003 |
| 2018/0078719 A1 | 3/2018 | Spence et al. |

FOREIGN PATENT DOCUMENTS

| | | |
|---|---|---|
| DE | 10317268 A1 | 11/2004 |
| EP | 1138340 A2 | 10/2001 |
| EP | 1586345 A1 | 10/2005 |
| GB | 1448473 A | 9/1976 |
| GB | 2252515 A | 8/1992 |
| WO | WO-198602276 A1 | 4/1986 |
| WO | WO-1999047197 A1 | 9/1999 |
| WO | WO-2003035157 A1 | 5/2003 |
| WO | WO-2004096315 A2 | 11/2004 |
| WO | WO-2005097307 A1 | 10/2005 |
| WO | WO-2006024292 A1 | 3/2006 |
| WO | WO-2006026387 A2 | 3/2006 |
| WO | WO-2007038152 A2 | 4/2007 |
| WO | WO-2015033288 A1 | 3/2015 |
| WO | WO-2018071812 A1 | 4/2018 |

OTHER PUBLICATIONS

International Search Report for International Application No. PCT/US2008/008792 dated Dec. 18, 2008.

International Search Report for International Application No. PCT/US2016/025233 dated Jun. 9, 2016.

Partial International Search Report for International Application No. PCT/US2007/021469 dated Jul. 10, 2008.

Supplementary Partial European Search Report dated Jan. 27, 2015 for European Application No. EP08780252.6.

U.S. Appl. No. 12/175,853 of Feline V. Cortez et al., filed Jul. 18, 2008.

U.S. Appl. No. 12/175,861 of Feline V. Cortez et al., filed Jul. 18, 2008.

U.S. Appl. No. 12/175,899 of Feline V. Cortez et al., filed Jul. 18, 2008.

Vapotherm, "The New Standard in High Flow Therapy Brochure," 6 pages (undated).

Doshi et al., "The ventilatory effect of high velocity nasal insufflation compared to non-invasive positive-pressure ventilation in the treatment of hypercapneic respiratory failure: a subgroup analysis," Heart & Lung, vol. 49: 610-615 (2020).

Möller et al., "Nasal High Flow Reduces Dead Space," Manuscript, Articles in Press. J Appl Physio, pp. 1-25 (Nov. 17, 2016).

Ram et al., "Non-invasive positive pressure ventilation for treatment of respiratory failure due to exacerbations of chronic obstructive pulmonary disease (Review)," Cochrane Library, The Cochrane Collaboration, Cochrane Database of Systematic Reviews, pp. 1-58 (2010).

Vital et al., "Non-invasive positive pressure ventilation (CPAP or bilevel NPPV) for cardiogenic pulmonary oedema (Review)," Cochrane Library, The Cochrane Collaboration, Cochrane Database of Systematic Reviews, pp. 1-139 (2013).

https://my.clevelandclinic.org/health/diseases/15283-acute-respiratory-distress-syndrome-ards Jun. 20, 2020.

https://lunginstitute.com/lung-diseases/copd/copd-and-acute-respiratory-distress-syndrome/#:~:text=ARDS%20can%20be%20brought%20on.at%20high%20risk%20of%20ARDS (2020).

Qin, et al., "Mesenchymal stem cell therapy for acute respiratory distress syndrome: from basic to clinics". Protein Cell 2020 11(10): 707 (707-722).

Rawal et al. "Acute respiratory distress syndrome: An update and review." Journal of Translational Internal Medicine. Apr.-Jun. 2018, vol. 6, Issue 2. p. 74 (pp. 74-77).

Shafiee et al. "Coronavirus disease 2019: A tissue engineering and regenerative medicine perspective." Stem Cells Transl. Med. 2020:1-12.

Doshi et al., "High-Velocity Nasal Insufflation in the Treatment of Respiratory Failure: A Randomized Clinical Trial", Annals of Emergency Medicine, Jul. 2017;72(1):73-83.

Spivey S., et al., "Assessment of High Flow Nasal Cannula Therapy use in the Emergency Department Setting: Observations of Practice Across Four Systems", Respiratory Therapy, vol. 10, No. 1, pp. 30-34 (2015).

* cited by examiner

SYSTEMS AND METHODS FOR HIGH VELOCITY NASAL INSUFFLATION

CROSS-REFERENCE TO RELATED APPLICATIONS

This application claims priority to U.S. provisional application No. 62/408,560, filed Oct. 14, 2016, the content of which is hereby incorporated herein by reference in its entirety.

BACKGROUND

Patients with respiratory ailments are often treated with respiratory assist devices that deliver supplemental breathing gas to the patient. Such devices may deliver gas to the patient using high flow therapy (HFT). HFT devices deliver breathing gas at a high flow rate via an interface such as a nasal cannula to increase the patient's fraction of inspired oxygen (FiO2), decrease the patient's work of breathing, or do both. That helps the patient recover from respiratory ailments, such as respiratory distress or bronchospasms. Some HFT devices heat and humidify the delivered breathing gas for medical reasons (e.g., to maintain the pliability of the tissues of surfactant-deficient patients, or to preserve mucosal integrity) or to reduce patient discomfort.

Some high flow therapy systems use membrane humidification to humidify the breathing gasses. The use of a membrane humidifier increases the pressure requirements of the system because membrane humidifiers resist the flow of air more than non-membrane humidifiers. Furthermore, conventional high flow therapy systems use nasal cannulas with small bore nasal prongs to increase the velocity of the breathing gasses entering a patient's airway. However, such cannulas further increase the required pressure compared to a system using large bore nasal prongs or a face mask. These increased pressure requirements of conventional high flow therapy systems necessitate the use of wall air or a large compressor which limits the potential field of use of high flow therapy.

Some respiratory therapy devices use a blower and a non-membrane humidifier to create humidified high flow therapy. Such non-membrane humidifiers are essentially heated water vessels through which gasses are channeled. These blower-based systems use larger bore cannulas to further reduce pressure requirements. However, large bore cannulas do not flush $CO_2$ as effectively from a patient's airway as do small bore cannulas. Furthermore, non-membrane humidifiers may produce lower quality vapor.

SUMMARY

Systems, devices, and methods for humidifying a breathing gas are presented. The system includes a base unit, a vapor transfer unit, a nasal cannula, and a liquid container. The base unit includes a blower. The vapor transfer unit is external to the base unit and includes a gas passage, a liquid passage, a gas outlet, and a membrane separating the gas passage and the liquid passage. The membrane permits transfer of vapor into the gas passage from liquid in the liquid passage. The nasal cannula is coupled to the gas outlet of the vapor transfer unit. The liquid container is configured to reversibly mate with the base unit.

The systems, devices, and methods presented herein have a low pressure system architecture which permits the system to be operated by a low pressure source (e.g., <275 kPa, <200 kPa, <150 kPa, <100 kPa, <50 kPa, <30 kPa, <20 kPa, <10 kPa, or any other suitable gauge pressure). In some implementations, the system is operated by a blower, such as a centrifugal blower. By using a blower or a similar low pressure source, the base unit does not require an external source of high pressure gas. Instead, the base unit can accept gas at ambient pressure and then pressurize the gas (e.g., internally). This allows the base unit to function in environments in which pressurized gas sources are not available (e.g., at home, in an ambulance, and/or an outpatient care center). In some implementations, the low pressure gas source can accept oxygen at a low pressure or at ambient pressure. This can enable the use of an oxygen concentrator rather than an oxygen tank.

The low pressure operation of the system is enabled at least in part by the low flow resistance of the vapor transfer unit. For example, at a flow rate of 40 LPM, the flow resistance of the vapor transfer unit may be <70 kPa, <60 kPa, <50 kPa, <40 kPa, <30 kPa, <25 kPa, <20 kPa, <15 kPa, <10 kPa, <5 kPa, <4 kPa, <3 kPa, <2 kPa, <1 kPa, or any other suitable flow resistance. Furthermore, in some implementations, the nasal cannula has a relatively short length and has separate flow paths for each nasal prong to lower the flow resistance of the system. In certain implementations, to further reduce the flow resistance, the system uses a large bore delivery tube to carry the output breathing gas from the low pressure source to the vapor transfer unit. In some implementations, the inner diameter of the delivery tube is more than about 5 mm. In certain implementations, the inner diameter of the delivery tube is about 15 mm.

In certain implementations, the liquid container has a lower surface formed of a flexible film. In some implementations, the liquid container couples to the base unit using a breech lock. A combination of breech lock and a lower surface formed of a flexible film may make inadvertent disconnection of the liquid container more difficult during operation. This is because when liquid is in the liquid container, the liquid exerts pressure against the film, which in turn exerts pressure against the breech lock, causing friction. Friction makes the breech lock more resistant to torque and thus more difficult to inadvertently disconnect during operation.

In some implementations, the liquid is heated and circulated within the liquid container without contacting the base unit. This can permit the base unit to be reused with lower risk of contamination compared to liquid-contacting base units.

In certain implementations the blower delivers breathing gas to the gas passage of the vapor transfer unit via a delivery tube and the liquid container delivers liquid to the liquid passage of the vapor transfer unit via a liquid delivery line disposed within the delivery tube. (The liquid container may also receive a return flow of liquid from the vapor transfer unit.) Since the delivery tube surrounds the liquid delivery line, the delivery tube insulates the liquid delivery line from ambient air. The liquid delivery line may carry heated liquid, so insulating the line can reduce the energy required to maintain the temperature of the line and thus reduce the energy requirements of the system. Moreover, some of the heat that is "lost" from the liquid delivery line in the delivery tube enters the flow of breathing gas. This warms the breathing gas, which later facilitates the transfer of vapor into the breathing gas at the vapor transfer unit. Thus, some of the heat "lost" from the liquid lines is still conserved within the breathing circuit. Additionally, in some implementations, the blower delivers heated gas through the delivery tube. In such implementations, the heated gas heats the liquid in the liquid delivery line, thus reducing the power demand on a liquid heater.

Furthermore, by permitting the delivery tube to surround the liquid delivery line, the system reduces the number of separate tubes that must be managed by the user. In conventional respiratory therapy systems in which a liquid container is separate from a breathing gas source, the user may have to manage two sets of tubes: tubes from the liquid container to the humidifier as well as tubes from the breathing gas source to the humidifier. In a system according to certain implementations disclosed herein, the gas path and the liquid path are integrated within a single tube. This reduces the amount of space occupied by tubing and reduces the risk of snagging the tubing inadvertently.

Additionally, disposing the liquid delivery line within the delivery tube reduces the risk of kinking the liquid delivery line. This is because the bend radius of the delivery tube limits the minimum bend radius of the liquid delivery line. For example, in some implementations, the delivery tube is corrugated, and corrugated tubing generally bends with a consistent radius on the inside of the bend.

According to one aspect, the system includes a base unit, a vapor transfer unit, a nasal cannula, and a liquid container. The base unit includes a blower. The vapor transfer unit is external to the base unit and includes a gas passage, a liquid passage, a gas outlet, and a membrane separating the gas passage and the liquid passage. The membrane permits transfer of vapor into the gas passage from liquid in the liquid passage. The nasal cannula is coupled to the gas outlet. The liquid container is configured to reversibly mate with the base unit.

In some implementations, the liquid container interlocks with a surface of the base unit. In certain implementations, the container has a surface formed of a flexible film. In some implementations, the base unit further includes a heating element for heating liquid, the heating element having a heating surface. In certain implementations, the flexible film is configured to mate with the heating surface when the liquid container mates with the base unit.

In some implementations, the blower is configured to pressurize breathing gas to less than about 276 kPa (40 psi). In certain implementations, the liquid container includes an impeller. In some implementations, the base unit includes a motor. In certain implementations, the motor is magnetically coupled to impeller. In some implementations, the liquid passage is coupled to the liquid container by a first tube. In certain implementations, the gas passage is coupled to the blower by a second tube. In some implementations, the first tube passes within the second tube.

In certain implementations, the base unit includes a pressure sensor configured to measure pressure of the liquid in the liquid container when the liquid container is coupled to the base unit. In some implementations, the pressure sensor is configured to measure pressure against the flexible film. In certain implementations, the second tube has an inner diameter of more than about 5 mm. In some implementations, the membrane is non-porous. In certain implementations, the nasal cannula includes an outlet having a cross sectional area less than a cross sectional area of a patient's nostril.

In some implementations, the base unit further includes an oxygen sensor. In certain implementations, the system includes an oxygen source. In some implementations, the system includes an oxygen concentrator. In certain implementations, the oxygen source includes an oxygen outlet, the blower includes a blower inlet, and the oxygen outlet is coupled to the blower inlet. In some implementations, the oxygen outlet is coupled to the blower inlet by a needle valve. In certain implementations, the blower includes a blower outlet, the liquid container includes a liquid inlet and a liquid outlet, and the liquid inlet and the liquid outlet are each spaced from the blower outlet by at least 10 cm.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
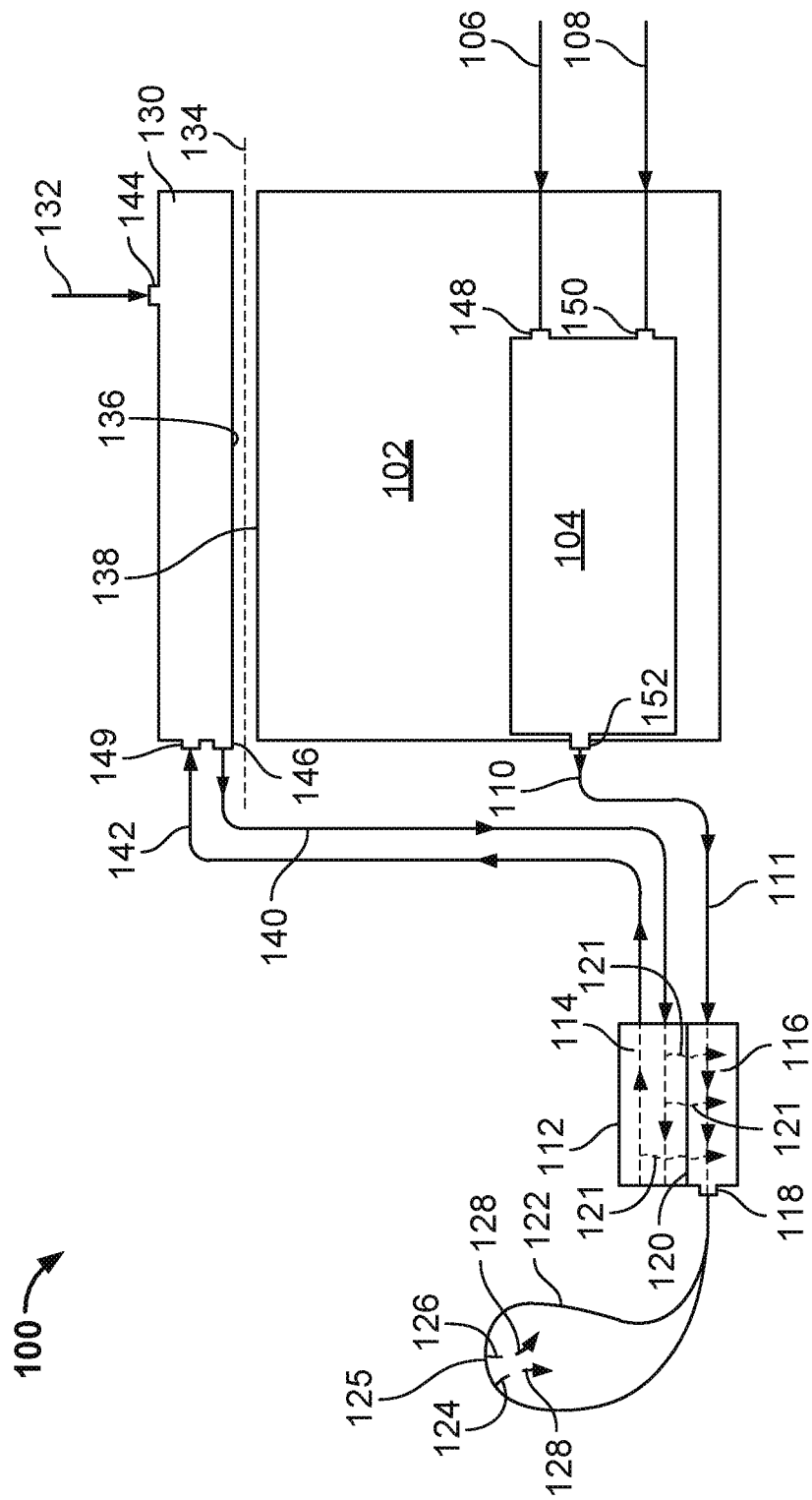
FIG. 1 shows an illustrative respiratory therapy system.

To provide an overall understanding of the systems, devices, and methods described herein, certain illustrative embodiments will be described. Although the embodiments and features described herein are specifically described for use in connection with a high flow therapy system, it will be understood that all the components and other features outlined below may be combined with one another in any suitable manner and may be adapted and applied to other types of respiratory therapy and respiratory therapy devices, including mechanical ventilation, continuous positive airway pressure therapy (CPAP), oxygen masks, Venturi masks, low flow oxygen therapy, tracheotomy masks, and the like.

Systems, devices, and methods for humidifying a breathing gas are presented. The system includes a base unit, a vapor transfer unit, a nasal cannula, and a liquid container. The base unit includes a blower. The vapor transfer unit is external to the base unit and includes a gas passage, a liquid passage, a gas outlet, and a membrane separating the gas passage and the liquid passage. The membrane permits transfer of vapor into the gas passage from liquid in the liquid passage. The nasal cannula is coupled to the gas outlet of the vapor transfer unit. The liquid container is configured to reversibly mate with the base unit.

The systems, devices, and methods presented herein have a low pressure system architecture which permits the system to be operated by a low pressure source (e.g., <275 kPa, <200 kPa, <150 kPa, <100 kPa, <50 kPa, <30 kPa, <20 kPa, <10 kPa, or any other suitable gauge pressure). In some implementations, the system is operated by a blower, such as a centrifugal blower. By using a blower or a similar low pressure source, the base unit does not require an external source of high pressure gas. Instead, the base unit can accept gas at ambient pressure and then pressurize the gas (e.g., internally). This allows the base unit to function in environments in which pressurized gas sources are not available (e.g., at home, in an ambulance, and/or an outpatient care center). In some implementations, the low pressure gas source can accept oxygen at a low pressure or at ambient pressure. This can enable the use of an oxygen concentrator rather than an oxygen tank.

The low pressure operation of the system is enabled at least in part by the low flow resistance of the vapor transfer unit. For example, at a flow rate of 40 LPM, the flow resistance of the vapor transfer unit may be <70 kPa, <60 kPa, <50 kPa, <40 kPa, <30 kPa, <25 kPa, <20 kPa, <15 kPa, <10 kPa, <5 kPa, <4 kPa, <3 kPa, <2 kPa, <1 kPa, or any other suitable flow resistance. Furthermore, in some implementations, the nasal cannula has a relatively short length and has separate flow paths for each nasal prong to lower the flow resistance of the system. In certain implementations, to further reduce the flow resistance, the system uses a large bore delivery tube to carry the output breathing gas from the low pressure source to the vapor transfer unit. In some implementations, the inner diameter of the delivery tube is more than about 5 mm. In certain implementations, the inner diameter of the delivery tube is about 15 mm.

In certain implementations, the liquid container has a lower surface formed of a flexible film. In some implementations, the liquid container couples to the base unit using a breech lock. A combination of breech lock and a lower surface formed of a flexible film may make inadvertent disconnection of the liquid container more difficult during operation. This is because when liquid is in the liquid container, the liquid exerts pressure against the film, which in turn exerts pressure against the breech lock, causing friction. Friction makes the breech lock more resistant to torque and thus more difficult to inadvertently disconnect during operation.

In some implementations, the liquid is heated and circulated within the liquid container without contacting the base unit. This can permit the base unit to be reused with lower risk of contamination compared to liquid-contacting base units.

In certain implementations the blower delivers breathing gas to the gas passage of the vapor transfer unit via a delivery tube and the liquid container delivers liquid to the liquid passage of the vapor transfer unit via a liquid delivery line disposed within the delivery tube. (The liquid container may also receive a return flow of liquid from the vapor transfer unit.) Since the delivery tube surrounds the liquid delivery line, the delivery tube insulates the liquid delivery line from ambient air. The liquid delivery line may carry heated liquid, so insulating the line can reduce the energy required to maintain the temperature of the line and thus reduce the energy requirements of the system. Moreover, some of the heat that is "lost" from the liquid delivery line in the delivery tube enters the flow of breathing gas. This warms the breathing gas, which later facilitates the transfer of vapor into the breathing gas at the vapor transfer unit. Thus, some of the heat "lost" from the liquid lines is still conserved within the breathing circuit. Additionally, in some implementations, the blower delivers heated gas through the delivery tube. In such implementations, the heated gas heats the liquid in the liquid delivery line, thus reducing the power demand on a liquid heater.

Furthermore, by permitting the delivery tube to surround the liquid delivery line, the system reduces the number of separate tubes that must be managed by the user. In conventional respiratory therapy systems in which a liquid container is separate from a breathing gas source, the user may have to manage two sets of tubes: tubes from the liquid container to the humidifier as well as tubes from the breathing gas source to the humidifier. In a system according to certain implementations disclosed herein, the gas path and the liquid path are integrated within a single tube. This reduces the amount of space occupied by tubing and reduces the risk of snagging the tubing inadvertently.

Additionally, disposing the liquid delivery line within the delivery tube reduces the risk of kinking the liquid delivery line or the delivery tube. This is because the delivery tube shields the liquid line from kinking by increasing the minimum bend radius that the liquid line undergoes during extreme bending. In some implementations, the delivery tube is corrugated to prevent or reduce kinking of the delivery tube or the liquid line.

FIG. 1 shows an illustrative respiratory therapy system 100 according to some implementations. The respiratory therapy system 100 includes a base unit 102, a liquid container 130, a vapor transfer unit 112, and a nasal cannula 122. The base unit 102 includes a blower 104 and an upper surface 138. The blower 104 includes an air inlet 148, which receives ambient air 106, and an oxygen inlet 150, which receives oxygen 108. The blower 104 also includes a blower outlet 152, through which breathing gas 110 exits. The liquid container 130 includes a first liquid inlet 144, a second liquid inlet 149, a liquid outlet 146, and a lower surface 136. The liquid container 130 reversibly couples to the base unit 102 at an interface 134. The vapor transfer unit 112 includes a liquid passage 114, a gas passage 116, a vapor transfer membrane 120, and a gas outlet 118. The vapor transfer unit 112 is coupled to the gas outlet 152 by a gas delivery tube 111. The nasal cannula 122 includes a nasal cannula body 125 and nasal prongs 124 and 126.

The base unit 102 delivers output breathing gas 110 to the vapor transfer unit 112 using the blower 104. By using the blower 104, the base unit 102 does not require an external source of pressurized gas. Instead, the base unit 102 can accept gas at ambient pressure. This allows the base unit 102 to function in environments in which pressurized gas sources are not available (e.g., at home, in an ambulance, and/or an outpatient care center). The base unit 102 is sized for convenient use in a variety of environments, including in a hospital or at home. For example, in some implementations, the base unit 102 is sized to sit on a conventional bed nightstand. In some implementations, the base unit 102 is configured to mount to an IV pole for use in a health care environment. The base unit 102 may be powered by a wall outlet, battery, other suitable power source, or any suitable combination of power sources.

The blower 104 receives air 106 through the air inlet 148 and receives oxygen 108 through the oxygen inlet 150. The blower 104 delivers output breathing gas 110 through the outlet 152. Although blending of oxygen and air is shown, in some implementations, the blower receives only air 106. For example, certain patients may not require oxygen therapy or oxygen sources may be unavailable in some settings. Although the air 106 and oxygen 108 are mixed within the blower 104 as depicted, in some implementations the air 106 and the oxygen 108 are mixed upstream of the blower 104. In certain implementations, the air 106 and the oxygen 108 are mixed downstream of the blower 104.

In some implementations, the blower 104 pressurizes the output breathing gas 110 to an output pressure that is lower than conventional wall air pressure (e.g., <275 kPa, <200 kPa, <150 kPa, <100 kPa, <50 kPa, <30 kPa, <20 kPa, <10 kPa, or any other suitable gauge pressure). This low pressure operation is enabled by the low pressure architecture of system 100, in particular the relatively low resistance of the breathing gas delivery tubing, vapor transfer unit 112, and nasal cannula 122, as will be discussed further below. In certain implementations, the blower 104 is a centrifugal blower.

The liquid container 130 delivers liquid (e.g., water) to the vapor transfer unit 112 through the liquid outlet 146. The liquid container 130 receives new liquid 132 through the liquid inlet 144 and receives recirculated liquid 142 from the vapor transfer unit 112 through the liquid inlet 149. The liquid container 130 may include a pump for driving the circulation of the liquid to and from the vapor transfer unit 112. In certain implementations, the liquid container includes a rotor which is driven by the base unit 102 to circulate the liquid within the liquid container. In certain implementations, the rotor is driven by the base unit 102 by a magnetic coupling. In some implementations, the circulation of the liquid may be driven by a pump external to the liquid container 130.

In some implementations, the liquid container 130 heats the liquid within the liquid container 130. In such imple-mentations, the heat may be generated by the base unit 102 and communicated from the upper surface 138 of the base unit to the lower surface 136 of the liquid container 130. The lower surface 136 of the liquid container may be formed of a material with high thermal conductivity and/or of a thin material. The lower surface 136 may be formed of a flexible film, which may improve the quality of contact of the lower surface 136 against the upper surface 138 compared to a rigid lower surface 136. In some implementations, the lower surface 136 is a flexible polymer.

In certain implementations, the base unit 102 measures the amount of liquid in the liquid container 130. In some implementations, the base unit measures the amount of liquid in the liquid container 130 by measuring the pressure of the liquid in the liquid container 130. The base unit 102 may measure this pressure through a force sensor, pressure sensor, and/or strain sensor disposed on the upper surface 138 of the base unit 102 which is in contact with the lower surface 136 of the liquid container 130. Although the liquid container 130 and the base unit 102 are shown interfacing at the upper surface 138 of the base unit 102 and the lower surface 136 of the liquid container 130, the skilled person will appreciate that the liquid container 130 can interface with the base unit 102 in other configurations. For example, in some implementations, the liquid container 130 couples to a lateral side of the base unit 102.

The vapor transfer unit 112 receives the gas 110 from the blower 104 and the liquid 140 from the liquid container 130 and delivers humidified gas through the gas outlet 118 to the nasal cannula 122. The gas 110 received by the vapor transfer unit 112 travels through the gas passage 116 before exiting the gas outlet 118. Simultaneously, the liquid 140 circulates within the liquid passage 114. Some of the liquid 140 diffuses across the vapor transfer membrane 120 and is converted to vapor 121. The vapor 121 is incorporated into the flow of gas 110 through the gas passage 116. The remainder of the liquid 120 returns to the liquid container 130 through the return path 142. In some implementations, the liquid 140 is water. In such implementations, the gas 110 is humidified in the gas passage 116 by the vapor 121.

The gas passage 116 of the vapor transfer unit 112 provides a relatively low flow resistance. For example, at a flow rate of 40 LPM, the flow resistance of gas through the vapor transfer unit 112 may be <70 kPa, <60 kPa, <50 kPa, <40 kPa, <30 kPa, <25 kPa, <20 kPa, <15 kPa, <10 kPa, <5 kPa, <4 kPa, <3 kPa, <2 kPa, <1 kPa, or any other suitable flow resistance. The low flow resistance of the vapor transfer unit 112 helps enable the low pressure operation of the system 100, which in turn enables the system to driven by a blower rather than a high pressure source.

The vapor transfer membrane 120 permits diffusion of the liquid 140 through the membrane 120 from the liquid passage 114 to the gas passage 116, where it becomes the vapor 121 and is absorbed into the gas 110 flowing through the gas passage 116. In some implementations, the vapor transfer membrane 120 is non-porous. In certain implementations, the vapor transfer membrane 120 is porous. In some implementations, the membrane 120 is a thermoplastic elastomer, a block copolymer, a polyether block amide, or any other suitable polymer. Although only a single vapor transfer membrane 120 is shown, in some implementations, the vapor transfer membrane 120 includes several membranes. For example, the vapor transfer membrane 120 may include a plurality of vapor transfer tubes or pleated sheets. Additional vapor transfer membrane designs compatible with the present disclosure are described in U.S. patent application Ser. No. 14/675,198, the contents of which are hereby incorporated by reference in their entirety.

The vapor transfer unit 112 is configured to be positioned proximate to the patient (e.g., within 10 feet, 6 feet, 3 feet, 2 feet, 1 foot, or 6 inches or the patient's airway), so as to reduce the length of tubing through which the humidified air has to travel to reach the patient. Since the inner diameter of tubing carrying heated and humidified gas must be relatively small to prevent condensation (e.g., 5 mm), reducing the length that the heated and humidified gas must travel reduces the length of the small diameter tubing. This reduces the resistance to air flow through the system, thereby enabling the system to operate at a lower pressure.

The nasal cannula 122 receives humidified breathing gas from the gas outlet 118 of the vapor transfer unit 112 and outputs the humidified breathing gas 128 through the nasal prongs 124 and 126. The nasal prongs 124 and 126 have a relatively small internal diameter to ensure a relatively high exit velocity of the breathing gas. In some implementations, the internal diameter of the nasal prongs 124 and 126 is <6 mm, <5 mm, <4 mm, <3 mm, <2 mm, or any other suitable diameter. A high exit velocity allows the breathing gas to better flush carbon dioxide from a patient's airways.

The nasal cannula 122 is configured to have a low flow resistance. For example, the nasal prong 124 and the nasal prong 126 each have separate gas flow paths which do not collide at the nasal cannula body 125. Furthermore, in some implementations, the nasal cannula 122 has a relatively short length to lower the flow resistance of the nasal cannula 112. In certain implementations, the nasal cannula 112 has a length of <2.5 m, <2 m, <1.5 m, <1 m, <0.5 m, or any other suitable length. Nasal cannula designs compatible with the present disclosure are disclosed in U.S. patent application Ser. No. 13/665,100, the contents of which are hereby incorporated by reference in their entirety.

To further reduce the flow resistance of the respiratory therapy system 100, the delivery tube 111, which carries the output breathing gas 110 from the blower 104 to the vapor transfer unit 112, has a relatively large inner diameter compared to conventional high flow therapy systems. In some implementations, the inner diameter of the delivery tube 111 carrying the breathing gas 110 is more than about 5 mm. In certain implementations, the inner diameter of the delivery tube 111 is about 15 mm. This larger diameter delivery tube 111 further reduces the pressure required to operate the respiratory therapy system 100 by reducing major head losses.

By using a low resistance vapor transfer unit 112, nasal cannula 122, and delivery tube 111, the respiratory therapy system 100 enables delivery of high velocity, humidified breathing gas with a relatively low pressure source, such as a blower (e.g., the blower 104). The use of a low pressure source enables the use of the system 100 in a variety of environments in which high pressure sources are not available (e.g., at home, in an ambulance, in an outpatient care facility).

Figure 2:
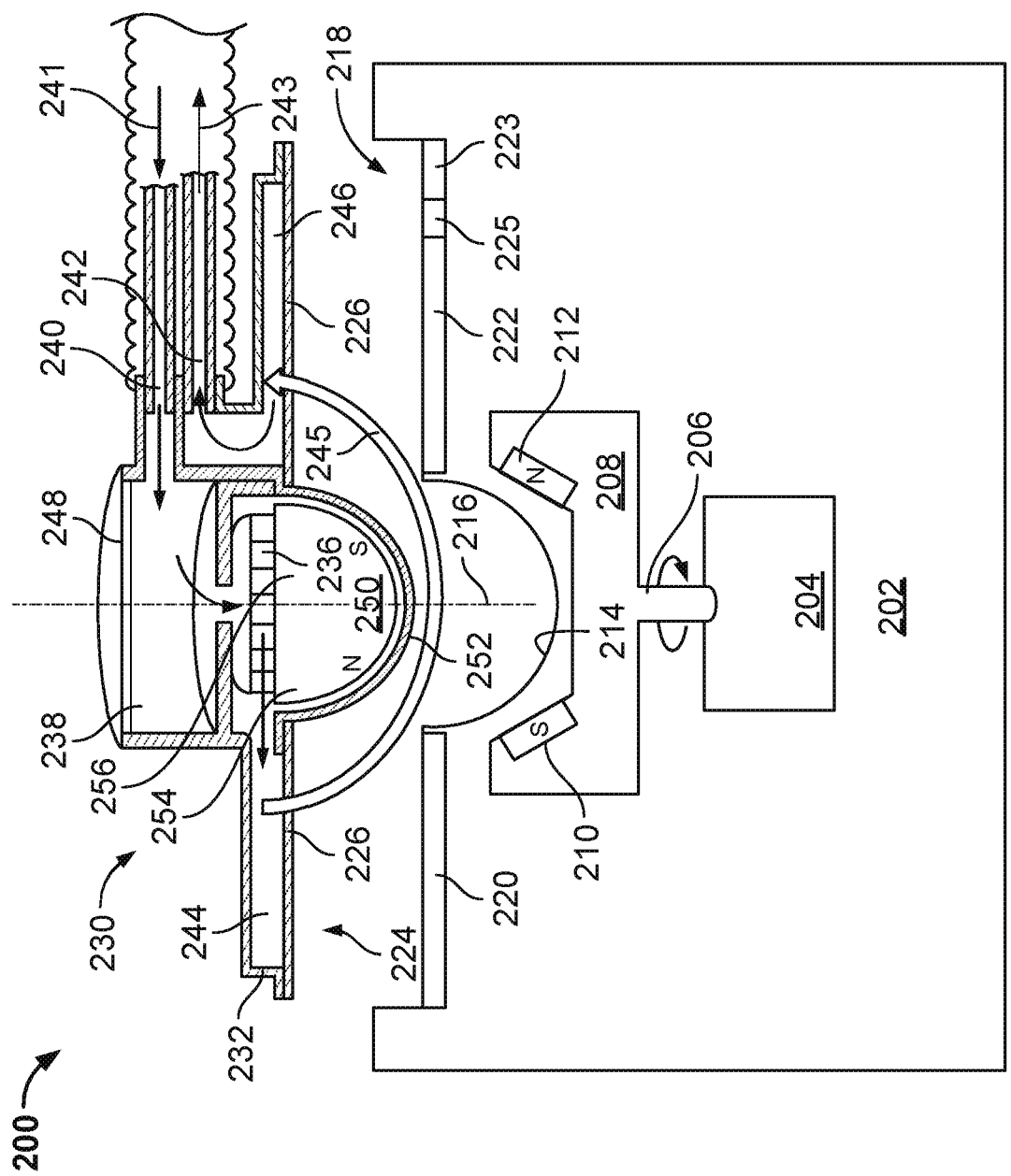
FIG. 2 shows an illustrative respiratory therapy system including a liquid container configured to heat and circulate liquid.

FIG. 2 shows an illustrative respiratory therapy system 200, according to some implementations, including a liquid container 230 configured to heat and circulate liquid. FIG. 2 only depicts the path of liquid in the system 200. The skilled person will appreciate that the liquid heating and circulation configuration depicted in FIG. 2 can be used with any suitable breathing gas circuit, including the breathing gas circuit disclosed in relation to FIG. 1.

The respiratory therapy system 200 includes a base unit 202 and the liquid container 230. The base unit 202 includes a motor 204, a drive shaft 206, a rotor 208, a recess 214, a mating surface 218, heating plate portions 220 and 222, a pressure sensor 223, and a temperature sensor 225. The rotor 208 has a rotational axis 216 and includes magnets 210 and 212. The liquid container 230 includes a body 232, a mating surface 224, cavities 244, 246, and 238, an inlet 240, an outlet 242, a membrane frit 248, an impeller 236, a magnet 250, a film 226, and a rotor cup 252. The magnet 250 includes a north pole 254 and a south pole 256.

The base unit 202 heats and circulates the liquid in the liquid container 230. The base unit heats the liquid in the liquid container using the heater plate portions 220 and 222. In some implementations, the heater plate portions 220 and 222 are different portions of a single, integral heater plate. The heater plate portions 220 and 222 are positioned against the mating surface 218 of the base unit 202. The mating surface 218 of the base unit 202 mates with the mating surface 224 of the liquid container 230. When the surfaces 218 and 224 are mated, the film 226 is positioned against the heater plate portions 220 and 222. The film 226 may have high thermal conductivity. In some implementations, the film 226 is flexible, which allows the film 226 to closely conform to the surface of the heater 220 to improve heat transfer.

The base unit 202 circulates the liquid in the liquid container 230 by a magnetic coupling between the rotor 208 and the magnet 250. The rotor 208 is driven by the motor 204 by the drive shaft 206. The rotor 208 rotates the magnets 210 and 212 about the axis 216. The magnets 210 and 212 are positioned in proximity to the recess 214. When the mating surface 224 of the liquid container 230 mates with the mating surface 218 of the base unit 202, the rotor cup 252 sits in the recess 214. When the rotor cup 252 sits within the recess 214, the magnet 250 magnetically couples with the magnets 210 and 212. The magnetic coupling between the magnet 250 and the magnets 210 and 212 enables the motor 204 to transfer rotation to the magnet 250.

The magnet 250 is physically coupled to the impeller 236 so that rotation of the magnet 250 results in rotation of the impeller 236. The impeller 236 is shaped so that rotation of the impeller 236 induces circulation of liquid within the liquid container 230. Rotation of the impeller 236 also draws in liquid 241 through the inlet 240 and into the cavity 238. While the liquid circulates within the liquid container 230, the membrane frit 248 allows gas trapped in the cavity 238 to escape into the atmosphere. Additionally, rotation of the impeller 236 moves liquid from the cavity 238 into the cavity 244 and then from the cavity 244 to the cavity 246 along a path 245. While the liquid moves along the path 245, it flows along the film 226. Since the film 226 is in contact with the heating plates 220 and 222 during operation, the liquid is heated while moving along the path 245. The movement of the liquid along the path 245 may improve heat transfer by increasing heat convection. Rotation of the impeller 236 also moves liquid from the cavity 246 to the outlet 242, where the liquid is expelled along a path 243. The liquid may be allowed to circulate multiple times before exiting the cavities 244 and 246.

Over the course of operating the system 200, the liquid may gradually be depleted as it is used to humidify breathing gas (not shown). Operating the system 200 with no liquid could lead to overheating. Accordingly, in some implementations, the base unit 202 senses when the liquid has been or is about to be depleted. In certain implementations, the presence of liquid in the liquid container 230 is sensed using the pressure sensor 223. When the mating surface 224 of the liquid container 230 mates with the mating surface 218 of the base unit 202, the film 226 sits against the pressure sensor 223. Since the film 226 is flexible, the pressure sensor can sense the pressure within the liquid container 230, particularly within the cavity 246, by measuring the deflection of the film 226. When the pressure measured at the film 226 drops, this indicates that the water level has fallen. This information can be used to shut off system 200 or to provide a warning to a user that the liquid container 230 needs to be replenished. The pressure sensor can be a strain gauge, a MEMS sensor, a force transducer, a piezoelectric sensor, or any other suitable sensor or combination thereof. In certain implementations, the absence or partial depletion of liquid can be detected by the temperature sensor 225. For example, if water is used as the liquid, the temperature sensor 225 may sense a steep rise in temperature (e.g., above the boiling point of water) when substantially all of the water is depleted. In some implementations, the pressure sensor 223 alerts the user when the force on the film 226 is low enough to allow easy removal of the liquid container 230 from a base unit. For example, the pressure sensor 223 may alert the user when a torque required to disengage a breech lock between the liquid container 230 and a base unit are below a predefined threshold (e.g., 20 Nm, 10 Nm, 5 Nm, 3 Nm, 2 Nm, 1 Nm, <1 Nm, or any other suitable threshold).

Figure 3:
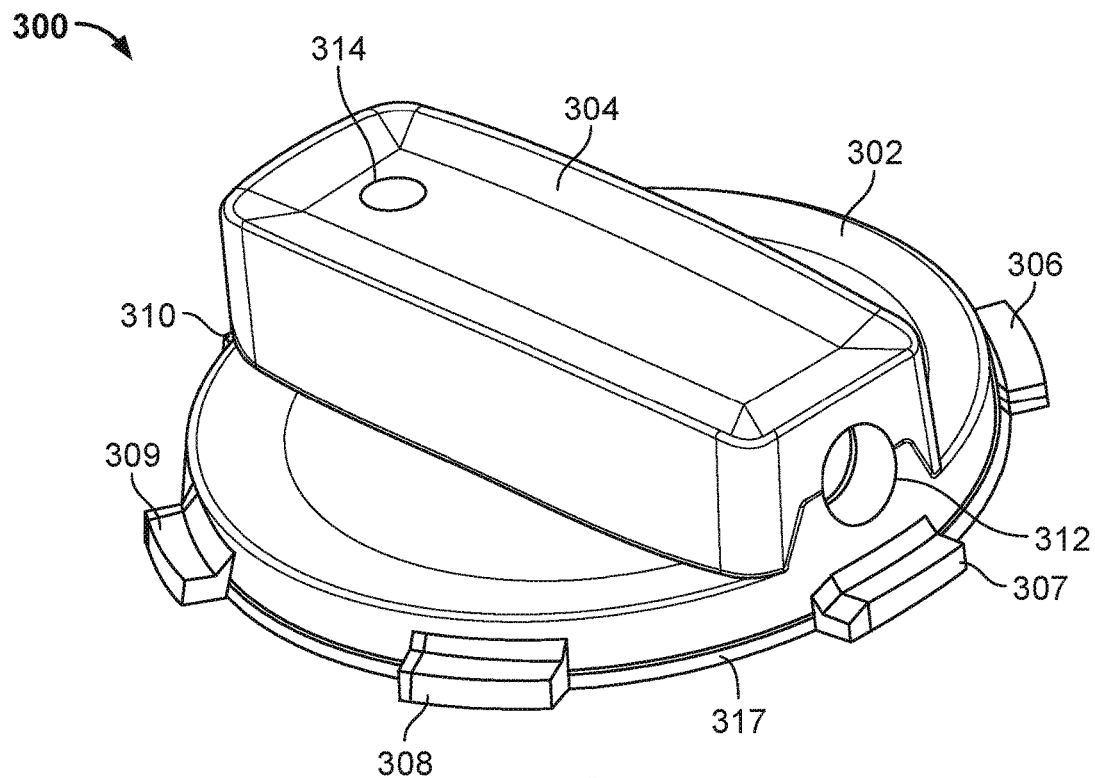
FIG. 3 shows an isometric view of an illustrative liquid container for a respiratory therapy system.
Figure 4:
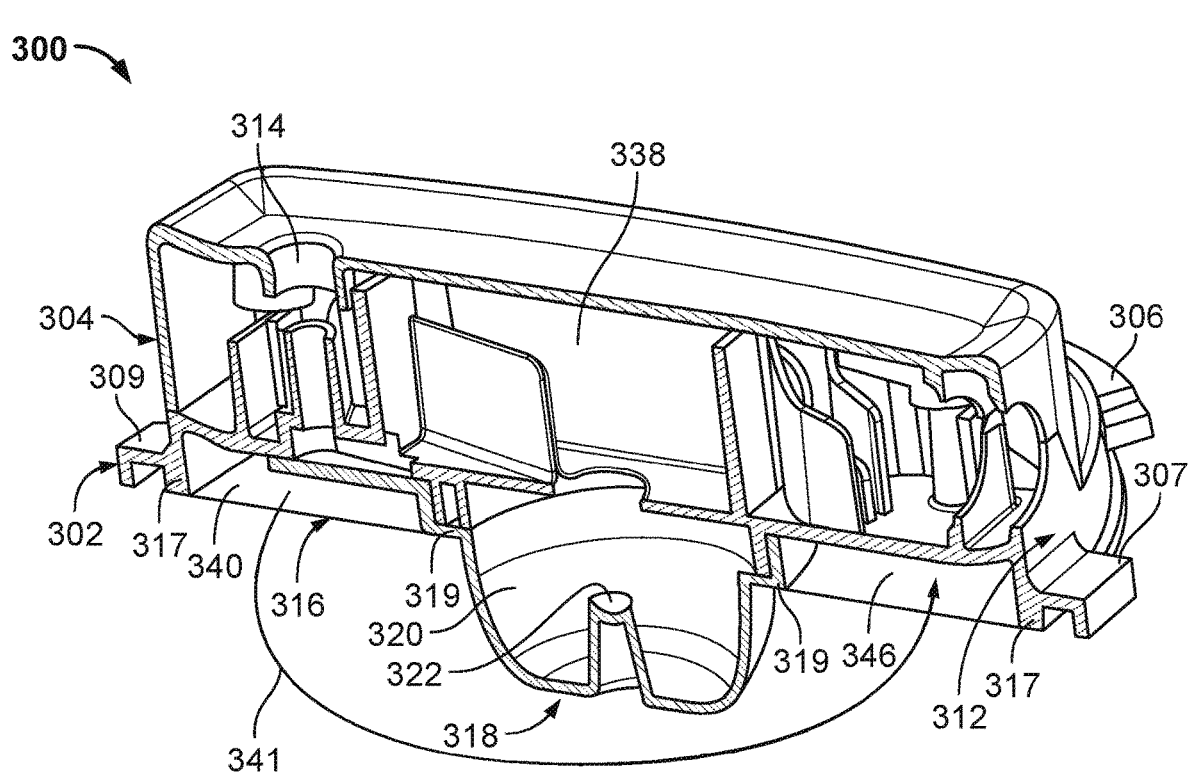
FIG. 4 shows an isometric cut-away view of the illustrative liquid container of FIG. 3.
Figure 5:
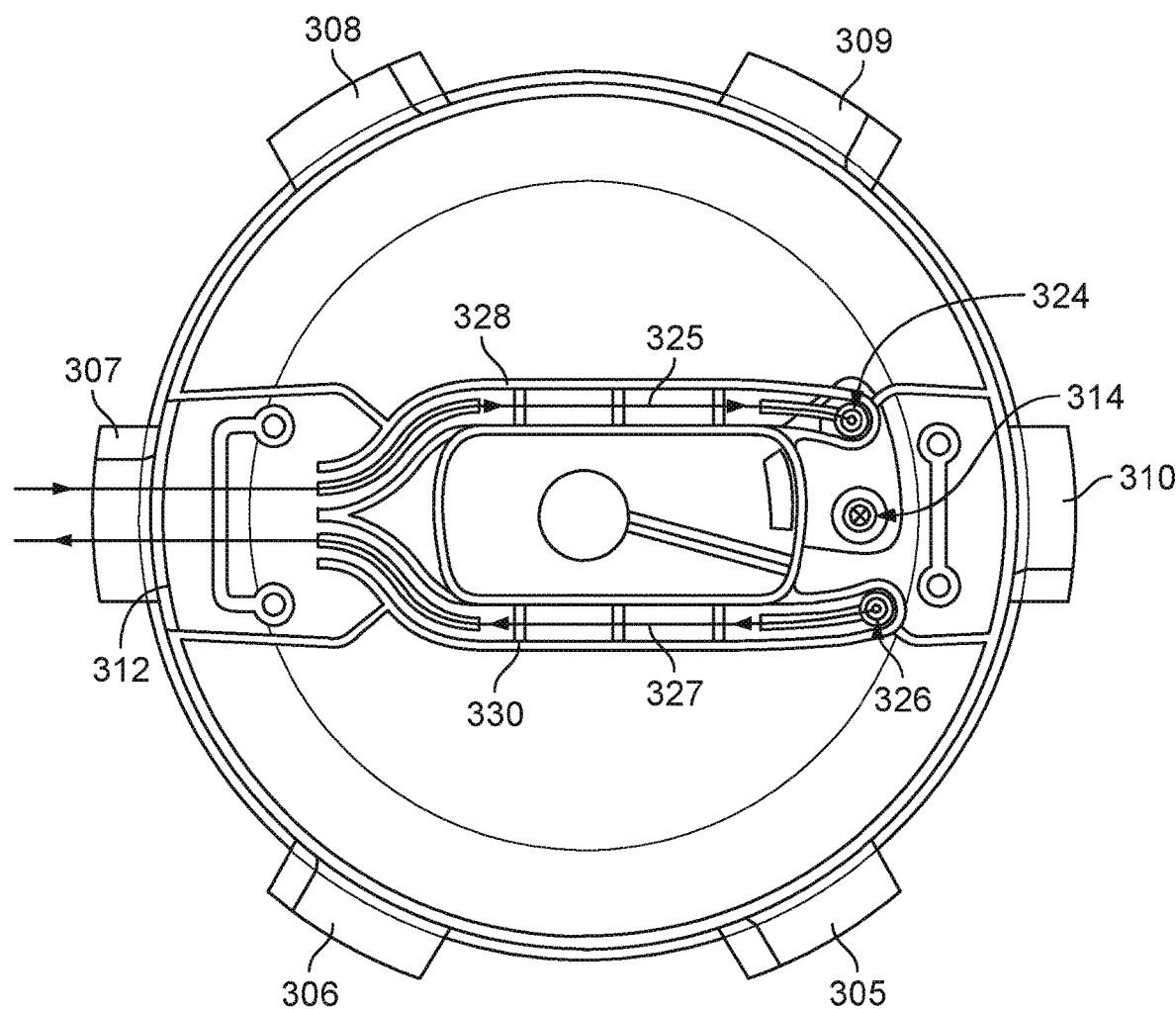
FIG. 5 shows a top view of a component of the illustrative liquid container of FIGS. 3 and 4.

FIGS. 3-5 show an illustrative liquid container 300 for a respiratory therapy system according to some implementations. FIG. 3 shows an isometric view of the liquid container 300, FIG. 4 shows an isometric cut-away view of the liquid container 300, and FIG. 5 shows a top view of the body 302 of the liquid container 300 with the cover 304 removed. The liquid container 300 may be used in the respiratory therapy system 100 of FIG. 1, the respiratory therapy system 200 of FIG. 2, or any other suitable respiratory therapy system. The liquid container 200 includes a body 302, a cover 304, a rotor cup 318, and a film 316. The body 302 includes breech lock tabs 305-310, a tubing port 312, an inlet 314, a lower rim 317, and cavities 348, 340, and 346. As visible in FIG. 5, the body 302 also includes a fluid inlet 324, a fluid outlet 326, and tubing paths 328 and 330. The rotor cup 318 includes a rim 319, a rotor cavity 320, and a bearing seat 322.

The liquid container 300 is depicted without tubing for clarity, but during use the liquid container 300 includes two tubes: a first tube connected to the inlet 324 and a second tube connected to the outlet 326. The first tube is held by the tubing path 328 and directs fluid along a path 325. The second tube is held by the tubing path 330 and directs fluid along a path 327.

The liquid container 300 receives liquid from a liquid source such as a water bag and then heats and circulates the liquid. The liquid container 300 initially receives liquid at the inlet 314. The inlet 314 is in fluid communication with the cavities 338, 340, and 346. The cavities 340 and 346 are bounded on the upper part by the body 302 and on the lower part by the film 316. The film 316 is joined in a fluid-tight manner to the lower rim 317 of the body 302 and the rim 319 of the rotor cup 318. Liquid in the cavities 340 and 346 may receive heat conducted across the film 316 by an external heater (e.g., heater plates 220 and 222 of system 200). Liquid in the cavities 340 and 346 may be circulated in the direction indicated by the arrow 341. This circulation may be induced by a rotor (not shown) disposed within the rotor cavity 320 (e.g., impeller 236 in system 200) or by any other suitable mechanism. The cavities 340 and 346 are also in fluid communication with the inlet 324 and the outlet 326 (shown in FIG. 5). The inlet 324 receives liquid returning from the vapor transfer unit (not shown) and passes such liquid to the cavity 338 like the liquid received via the inlet 314. The circulated liquid is expelled through the outlet 326.

The liquid container 300 is configured to mate with a base unit (e.g., the base unit 1002 of system 1000 of FIG. 10 below). To that end, the body 302 includes the breech lock tabs 305-310. The breech lock tabs 305-310 are disposed along the rim 317 of the body 302 and extend radially outward. The breech lock tabs 305-310 allow the liquid container 300 to be locked to a base unit with a twisting motion and unlocked by a similar twisting motion in the opposite direction. The breech lock design allows for simple and quick attachment to a base unit. Also, such an attachment mechanism is resistant to axial force, which may be developed by fluid pressure between the film 316 and the base unit. Additionally, the breech lock design may make inadvertent disconnection of the liquid container 300 more difficult during operation. This is because when liquid is in the cavities 340 and 346, the liquid exerts pressure against the film 316, which in turn exerts pressure against the base unit (not shown), causing friction. Friction makes the breech lock more resistant to being twisted open. Thus, when fluid is in the container 300 (i.e., during operation) the liquid container 300 is more difficult to inadvertently disconnect from the base unit.

The rotor cup 318 is dimensioned and configured to house a rotor for circulating liquid within the liquid container 300. In some implementations, the rotor cavity 320 of the rotor cup 318 houses a magnet for magnetically coupling with the base unit. The magnet may rotate on a bearing seated on the bearing seat 322. The bearing may be a spherical bearing, a hydrostatic bearing, a journal bearing, or any other suitable type of bearing.

By allowing liquid to be heated and circulated within the liquid container 300, the liquid container can avoid exposing the components of the base unit to the liquid. This can permit the base unit to be reused with lower risk of contamination compared to liquid-contacting base units. Such a configuration makes disposal and replacement of the liquid container 300 fairly simple.

Figure 6:
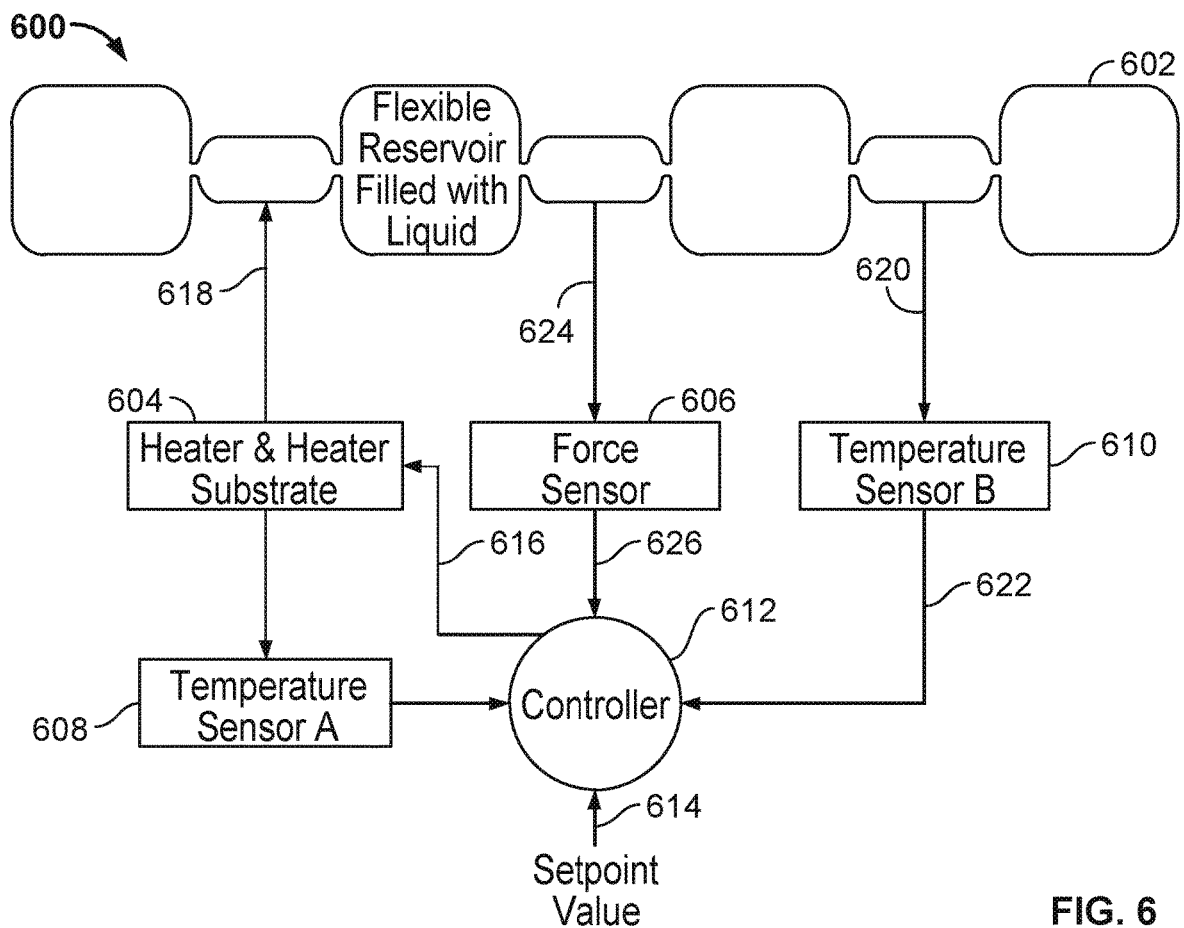
FIG. 6 shows an illustrative feedback control system for heating liquid for a respiratory therapy system.

FIG. 6 shows an illustrative feedback control system 600 for heating liquid for a respiratory therapy system according to some implementations. The feedback control system 600 includes a flexible reservoir 602, a heater and heater substrate 604, a force sensor 606, a temperature sensor 608, a temperature sensor 610, and controller 612. The controller 612 receives a set point value 614. The set point value 614 is a target temperature. Based on the set point value 614, the controller 612 generates a command value 616 and sends the command signal 616 to the heater and heater substrate 604. Upon receiving the command signal 616, the heater and heater substrate generate thermal energy 618 which is applied to the flexible reservoir 602. As the flexible reservoir receives thermal energy the liquid within it heats and the temperature of the flexible reservoir 602 increases. The temperature of the flexible reservoir 602 is measured by the temperature sensor 610. This temperature 622 is sent to the controller 612. Additionally, the temperature of the heater and heater substrate 604 is measured by the temperature sensor 608 which sends this temperature information to the controller 612 also. The controller 612 adjusts the command value 616 as necessary based on the temperature readings from the temperature sensor 608 and the temperature sensor 610. The controller 612 may operate using any suitable control algorithm. For example, in some implementations, the controller 612 is a PID controller. In certain implementations, the controller 612 is a simple hysteresis controller.

In addition to measuring temperature, the controller 612 also measures the pressure in the flexible reservoir 602. The controller 612 receives a signal 626 from the force sensor 606 which is indicative of the force 624 which is applied by the flexible reservoir on the force sensor 606. Measuring the pressure in the flexible reservoir 602 allows the controller 612 to determine the level of liquid (e.g., water) in the flexible reservoir. For example, the pressure measured by the force sensor may be approximately linearly related to the level of water in the flexible reservoir. According to the Bernoulli equation, the pressure of liquid at the bottom of a liquid column may be a function of the density of the liquid and the height of the liquid column. The skilled person will appreciate that the force measured at the force sensor 606 may be lower than the pressure in the flexible reservoir due to the elasticity of the flexible reservoir 602 which may absorb some of the internal pressure. However, the skilled person will appreciate that the force sensor measurement 626 can be adjusted to account for distortions due to the effect of the flexible reservoir 602 on the pressure measurement. Measuring the level of liquid in the flexible reservoir 602 allows the system 600 to detect when liquid has been depleted or is about to be depleted. Operating the system 600 with no liquid in the flexible reservoir 602 could lead to overheating and damage to the system 600. Therefore, measuring the level of liquid 602 can help avoid these unwanted outcomes.

The foregoing shows that the system 600 provides three layers of protection. First, the system 600 directly measures the heater temperature using the temperature sensor 608. This allows the system to detect if the heater 604 is overheating. If the temperature sensor 608 detects overheating of the heater 604, the controller 612 can send a command signal 616 to shut off the heater and heater substrate 604. In addition, the temperature sensor 610 allows the temperature 620 of the flexible reservoir 602 to be measured. This allows the controller 612 to detect if the flexible reservoir 602 is being overheated. If the flexible reservoir 602 is overheated, the controller 612 can again send a command signal 616 to shut off or reduce the power supplied to the heater and heater substrate 604. Third, the force sensor 606 allows the controller 612 to sense when the liquid in the flexible reservoir 602 has been depleted or is about to be depleted. This can also help avoid overheating. Additionally, the measurement 626 of the force sensor 606 allows the controller 612 to sense impending depletion of the flexible reservoir 602 before it actually occurs. This can allow time to provide a warning signal to a health care professional or user to replace liquid before any overheating occurs which could be detected by the temperature sensor 608 and the temperature sensor 610. Thus, the force sensor 606 complements the temperature sensors 608 and 610. The use of the force sensor 606 to detect the fluid level is enabled by the use of the flexible reservoir 602. A rigid reservoir may make measurement of the fluid level in the reservoir more difficult using non-contact means. Some high-flow therapy systems use floats to determine the level of liquid within a rigid reservoir. Such floats require more moving parts, which adds complexity and cost to the system. Furthermore, it is possible for floats to become jammed and therefore erroneously indicate a higher than actual water level.

Figure 7:
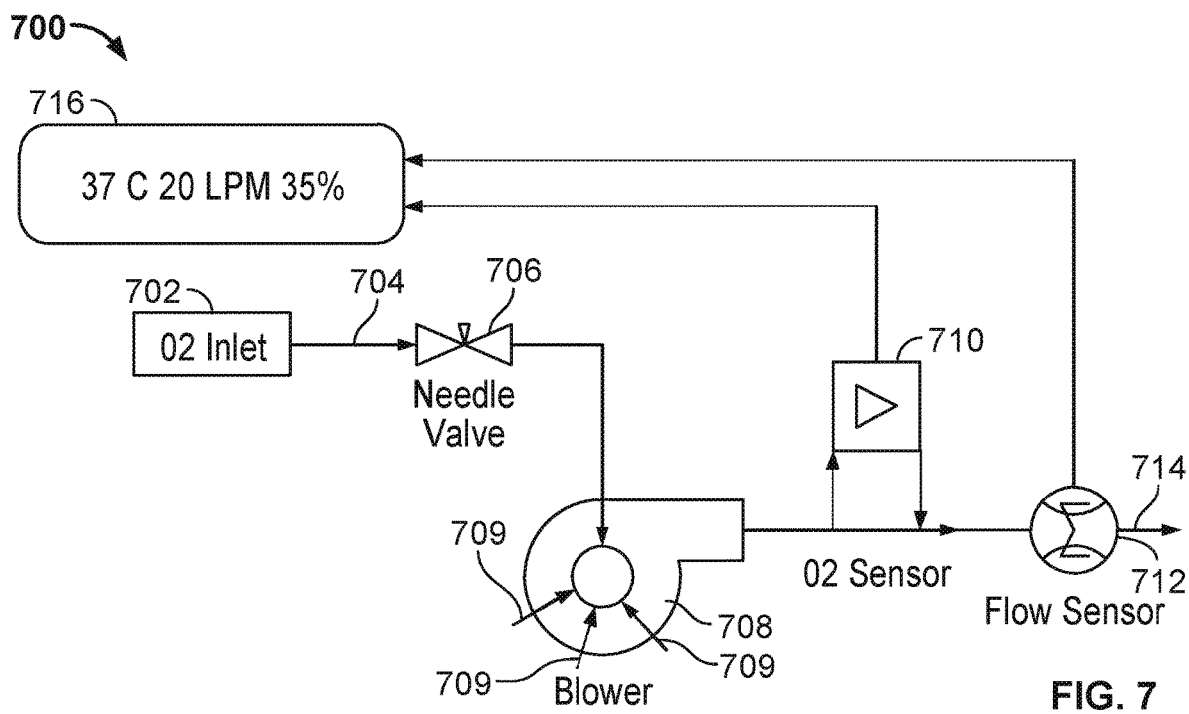
FIG. 7 shows an illustrative system for blending air and oxygen for respiratory therapy.

FIG. 7 shows an illustrative system 700 for blending air and oxygen for respiratory therapy according to some implementations. The system 700 includes an oxygen inlet 702, a needle valve 706, a blower 708, an oxygen sensor 710, a flow sensor 712, and a monitor 716. The oxygen inlet 702 feeds oxygen 704 to the needle valve 706. The oxygen inlet 702 can receive oxygen from any suitable source. For example, the oxygen inlet 702 can receive oxygen from an oxygen tank or an oxygen concentrator. Because the blower 708 is downstream from the oxygen inlet 702, the oxygen inlet 702 can accept a relatively low pressure or even ambient pressure oxygen source. This enables the use of an oxygen concentrator with the system 700. This is in contrast to some conventional high-flow therapy systems which require a high-pressure oxygen source. The oxygen 704 from the oxygen inlet 702 is fed to the needle valve 706. The needle valve 706 controls the amount of oxygen that is fed the blower 708 by allowing the flow resistance of the needle valve 706 to be adjusted by the user. The blower 708 draws oxygen from the needle valve 706. The blower also draws ambient air 709. The oxygen and ambient air are mixed and pressurized in the blower 708. In some implementations, the oxygen and air are mixed slightly upstream of the blower 708. In certain implementations, the oxygen and air are mixed downstream of the blower 708. The gas output by the blower 708 is fed past the oxygen sensor 710. The oxygen sensor senses the amount of oxygen in the output gas from the blower 708 and sends this information to the display 716. The oxygen measurement from the oxygen sensor 710 can be displayed on the display 716 while the user is adjusting the needle valve 706. This allows the user to have real-time feedback of the oxygen being delivered by the blower 708. This can allow for easy adjustment of the oxygen content and more precise adjustment of the oxygen content compared to conventional respiratory therapy systems. Conventional respiratory therapy systems relied on look up tables and manual adjustment of air and oxygen sources to maintain a target flow rate and oxygen fraction. This required the user to refer to a table or perform mathematical calculations and vary two dials together. The system 700 permits the user to set oxygen fraction using feedback displayed on the display 716 rather than a look up table and allows the user to adjust a single dial, namely the needle valve 706, to set the desired oxygen fraction. After passing the oxygen sensor the gas output of blower 708 passes the flow sensor 712. The flow sensor 712 also feeds to the display 716 so that the user can observe the flow rate. In the example of FIG. 7, the output gas 714 has a temperature of 37° Celsius, a flow rate of 20 meters per minute, and an oxygen fraction of 35%. The measure of the flow sensor 712 can be used to automatically adjust the speed of the blower 708 to maintain a constant flow rate set point. Since the blower 708 can be controlled by a feedback loop with the flow sensor 712, the blower 708 can be automatically controlled to maintain the set flow rate. This allows the user who wants to change oxygen fraction to only consider oxygen fraction without also considering changes in the flow rate. Again, this allows independent control of the oxygen fraction apart from the flow rate. By enabling oxygen to be controlled independently of flow rate in an easy fashion using the combination of the needle valve 706, blower 708, oxygen sensor 710, flow sensor 712, and display 716, the system 700 enables a more convenient user experience.

Figure 8:
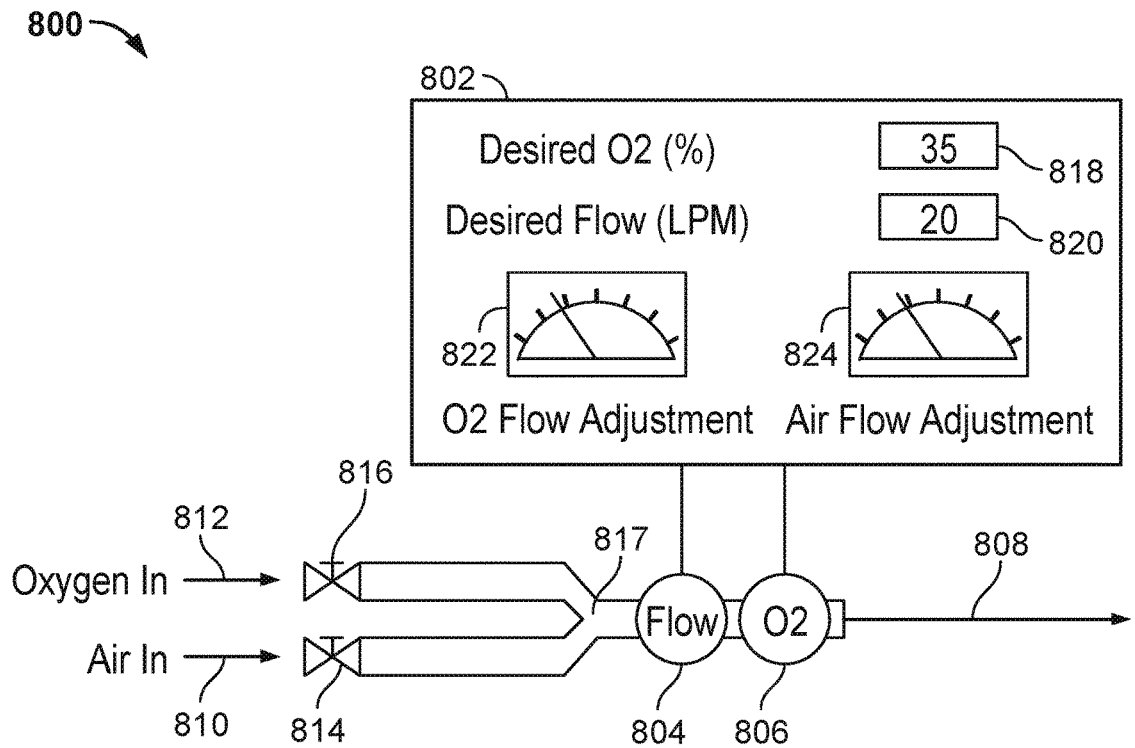
FIG. 8 shows an illustrative system for blending air and oxygen fore respiratory therapy using manually adjusted valves.

FIG. 8 shows an illustrative system for blending air and oxygen for respiratory therapy using two manually-adjusted values according to some implementations. While the system 700 involved adjusting a single valve manually, the system 800 involves adjusting two valves to control flow rate and oxygen fraction. The system 800 includes a manually-adjusted air valve 814, a manually-adjusted oxygen valve 816, an air-oxygen blender 817, a flow sensor 804, an oxygen sensor 806, and a software display system 802. The software display 802 includes an indicator of desired oxygen fraction 818, desired flow rate 820, suggested oxygen adjustment 822, and suggested air flow adjustment 824. The system 800 accepts oxygen 812 through the manually-adjusted oxygen valve 816 and accepts air 810 through the manually-adjusted air valve 814. The system 800 outputs blended gas 808 for delivery to the patient. In use, a user would enter the desired oxygen fraction 818 and desired flow rate 820 into the software display 802. In response, the software display 802 would indicate the necessary adjustments to the valves 814 and 816. This indication is made through the suggested oxygen flow adjustment 822 and the suggested air flow adjustment 824. The suggested oxygen flow adjustment 822 uses the input desired oxygen fraction 818 and desired flow rate 820 to generate an indication of the correct position of the manually-adjusted oxygen valve 816. The user would look to the suggestion 822 and adjust the oxygen valve 816 accordingly. Additionally, the suggested air flow adjustment 824 instructs the user how to manually adjust the air valve 814. The user would look to the air flow adjustment 824 to determine the correct position of the air valve 814. When the oxygen valve 816 and the air valve 814 are set to the suggested values 822 and 824, respectively, the output gas 808 should have the desired properties indicated in 818 and 820. To insure that the correct oxygen fraction in air flow rate have been achieved, the flow rate sensor 804 and oxygen sensor 806 provide feedback information which can be used to determine whether the recommended adjustments 822 and 824 need to be modified to actually achieve the desired properties 818 and 820. Further oxygen blending configurations compatible with the present disclosure are described in U.S. patent application Ser. No. 14/983,212, the contents of which are hereby incorporated by reference in their entirety.

Figure 9:
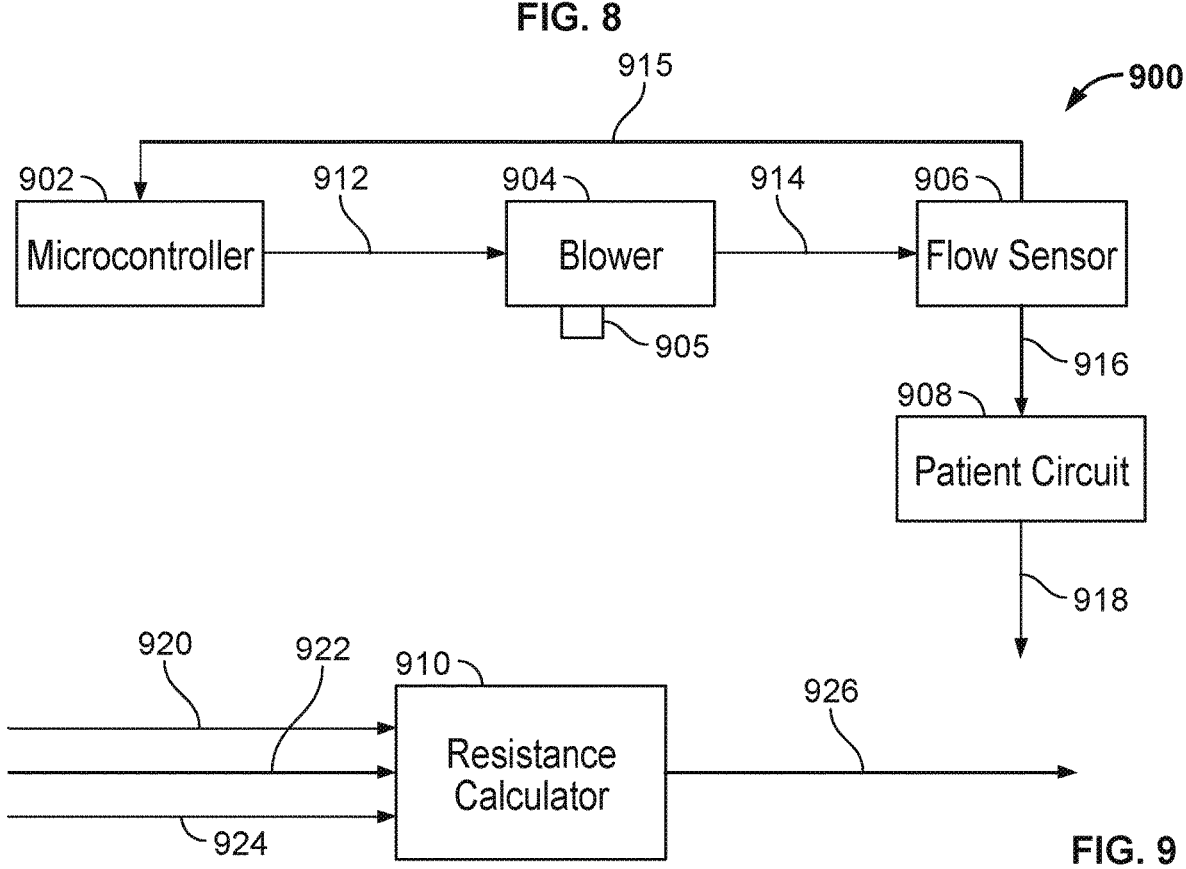
FIG. 9 shows an illustrative system for estimating the flow resistance of a respiratory therapy system.

FIG. 9 shows and illustrative system 900 for estimating the flow resistance of a respiratory therapy system according to some implementations. The system 900 included a micro-controller 902, a blower 904, a flow sensor 906, a patient circuit 908, and a resistance calculator 910. The micro-controller 902 uses a digital to analog converter to output a command signal 912 to the blower 904. The blower 904 includes a gas inlet 905. The blower 904 accepts gas at the gas inlet 905, pressurizes the gas, and outputs the pressurized gas as gas flow 914. The gas flow 914 is measured by the flow sensor 906. The flow rate information 915 is fed back to the micro-controller 902. The gas flow 916 exiting the flow sensor 906 enters the patient circuit 908. The gas flow 918 exits the patient circuit 908 and flows to the patient. The patient circuit 908 may include a gas delivery tube and a nasal cannula. The resistance calculator 910 receives the digital to analog conversion code 920, the flow sensor reading 922, and the error 924. From these three inputs, the resistance calculator 910 estimates the resistance of the patient circuit 908. The estimated resistance 926 is the output of the resistance calculator.

The estimated resistance 926 can be used to sense various conditions of the patient circuit 908. For example, the estimated resistance 926 can be used to determine an obstruction of the patient circuit 908. If the estimated resistance is unusually high, this may indicate that the patient circuit 908 is occluded. This occlusion could occur from the delivery to being kinked. If the estimated resistance 926 is unusually low, this may indicate that the nasal cannula has been disconnected, that the delivery tube has been disconnected, or a similar malfunction.

Figure 10:
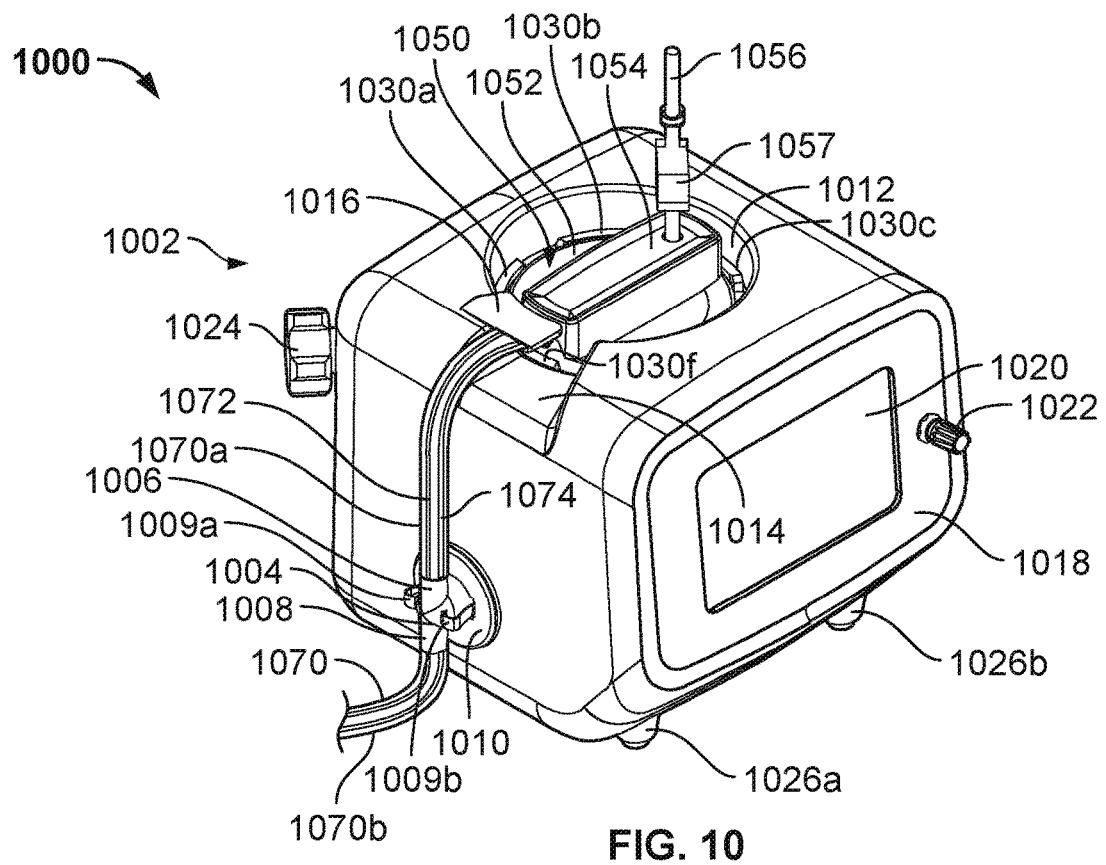
FIG. 10 shows an isometric view of an illustrative respiratory therapy system for high velocity nasal insufflation.
Figure 11:
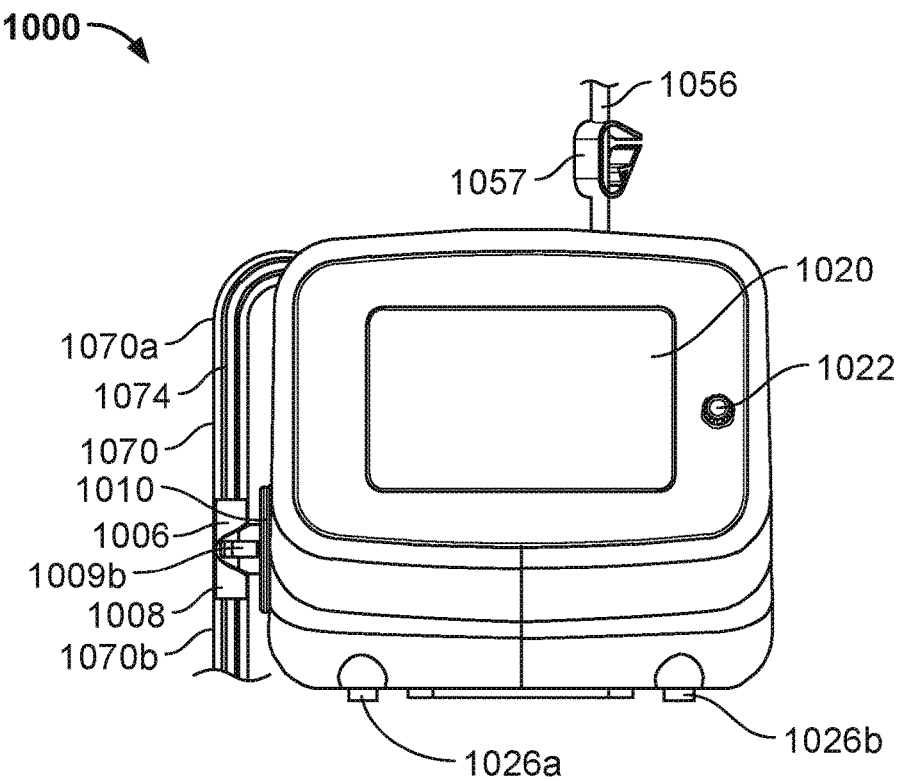
FIG. 11 shows a front view of the illustrative respiratory therapy system of FIG. 10.
Figure 12:
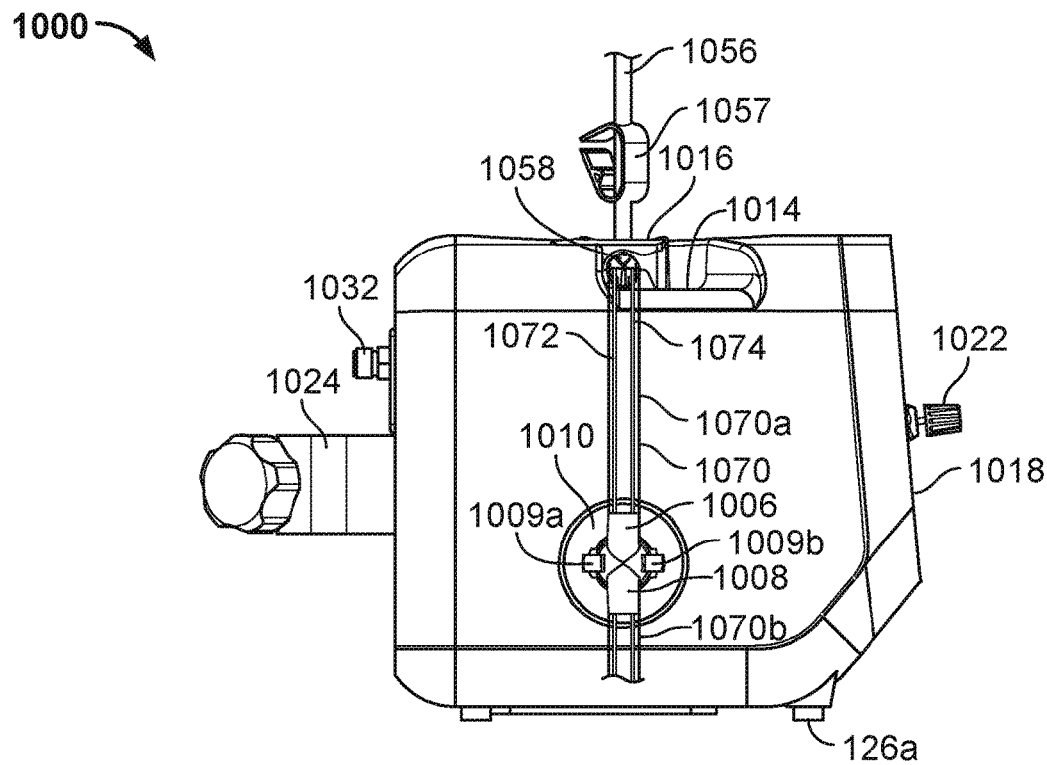
FIG. 12 shows a side view of the illustrative respiratory therapy system of FIGS. 10 and 11.
Figure 13:
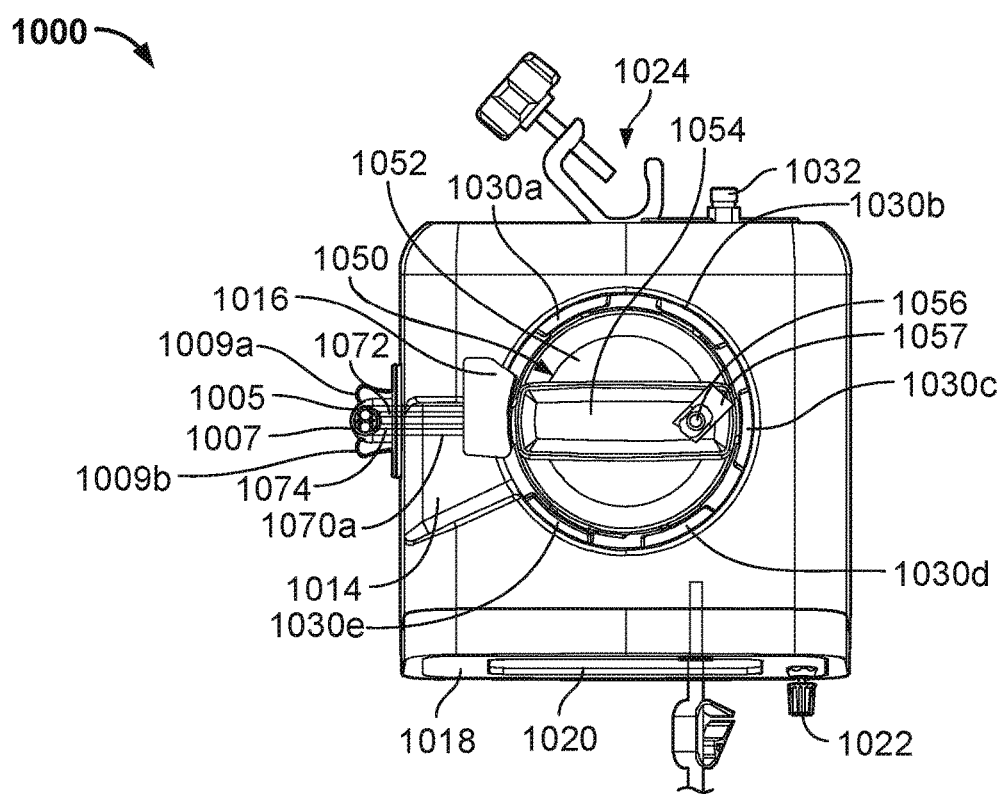
FIG. 13 shows a top view of the illustrative respiratory therapy system of FIGS. 10-12.
Figure 14:
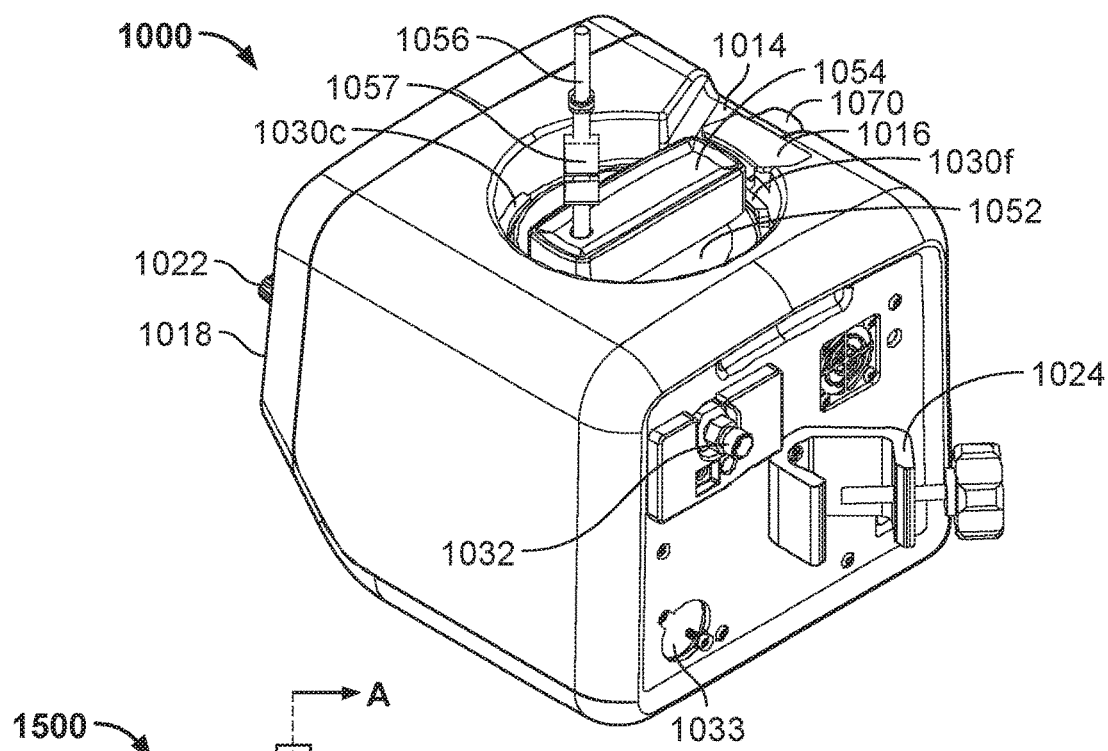
FIG. 14 shows a rear isometric view of the illustrative respiratory therapy system of FIGS. 10-12.

FIGS. 10-14 show an illustrative respiratory therapy system 1000 for high velocity nasal insufflation according to some implementations. FIG. 10 shows an isometric view of the respiratory therapy system 1000, FIG. 11 shows a front view of the respiratory therapy system 1000, FIG. 12 shows a side view of the respiratory therapy system 1000, FIG. 13 shows a top view of the respiratory therapy system 1000, and FIG. 14 shows a rear isometric view of the respiratory therapy system 1000. The respiratory therapy system 1000 includes a base unit 1002, a liquid container 1050, a liquid line 1056, a delivery tube 1070, and a delivery tube connector 1004. The base unit 1002 includes a recess 1012, retention flanges 1030a-f, a recess 1014, a retention tab 1016, an oxygen inlet 1032, an air inlet 1033, a front panel 1018, a display 1020, a needle valve knob 1022, a pole mount 1024, and feet 1026a-b. The liquid container 1050 includes a body 1052, and a cover 1054. The liquid line 1056 includes a clip 1057. The delivery tube 1070 includes an upstream tube portion 1070a, a downstream tube portion 1070b, a liquid delivery line 1072, and a liquid return line 1074. The delivery tube connector 1004 includes a base 1010, an upstream connector 1006, a downstream connector 1008, and wings 1009a-b.

The base unit 1002 is reversibly coupled to the liquid container 1050. The recess 1012 of the base unit 1002 accepts the body 1052 of the liquid container 1050. The recess 1014 of the base unit accepts the upstream portion 1070a of the delivery tube 1070 so that the delivery tube 1070 can connect to the liquid container 1050 while the liquid container 1050 is within the recess 1012. The retention flanges 1030a-f mate with breech lock tabs (not visible) on the liquid container 1050 to retain the liquid container 1050 within the recess 1014. Similar to the retention flanges 1030a-f, the retention tab 1016 mates with the upstream portion 1070a of the delivery tube 1070 to retain the delivery tube 1070 within the recess 1014. The retention tab 1016 does not extend across the entire recess 1014 so that the delivery tube 1070 can be removed from the recess 1014 by rotating and lifting the liquid container 1050 relative to the base unit 1002. In the implementation of FIG. 10, such removal can be achieved by rotating the liquid container 1050 counter clockwise. Although six retention flanges 1030a-f are depicted, any suitable number of retention flanges may be used (e.g., 1, 2, 3, 4, 5, 7, 8, >8 or any other suitable number). In some implementations, the liquid container 1050 is coupled to the base unit without the use of a breech lock configuration. For example, in certain implementations, the liquid container 1050 slides linearly into the base unit 1002 to interlock with the base unit. In certain implementations, the liquid container 1050 couples to the base unit 1002 by a friction fit, an interference fit, a snap fit, a mechanical fastener, a magnetic coupling, or any other suitable coupling.

The base unit 1002 receives air and/or oxygen and outputs pressurized gas. The base unit 1002 receives air through the air inlet 1033 and can receive oxygen through the oxygen inlet 1032 (visible in FIG. 14). The base unit 1002 includes a blower (not visible), which pressurizes the air and/or oxygen within the base unit 1002. The air inlet 1033 can receive ambient air at atmospheric pressure. The oxygen inlet 1032 can accept oxygen at atmospheric pressure or at a higher pressure. The oxygen inlet 1032 can accept oxygen from an oxygen concentrator.

The base unit 1002 allows the output of breathing gas to be controlled by a user via features of the front panel 1018. The front panel 1018 is angled slightly upward (best seen in FIG. 12). This allows a user to read and operate the front panel 1018 even when the base unit 1002 is positioned at a relatively low height (e.g., on a bedside night stand) or at a relatively high height (e.g., on an IV pole). The base unit 1002 can be supported by the feet 1026a-b when sitting on a horizontal surface, such as a night stand or other table. The base unit 1002 can be supported by the pole mount 1024 when mounted on an IV pole or any other pole.

The front panel 1018 includes the display 1020 and the needle valve 1022. In some implementations, the display 1020 is a touchscreen user interface. In certain implementations, the display 1020 presents the flow rate of breathing gas output, the oxygen fraction of breathing gas output, the temperature of breathing gas output, the flow rate set point, the oxygen fraction set point, the temperature set point, overheating warnings, flow occlusion warnings, low flow resistance warnings, liquid depletion warnings, and/or any other suitable information relevant to respiratory therapy.

The needle valve 1022 controls the amount of oxygen accepted through the oxygen inlet 1032. In some implementations, the needle valve 1022 restricts the flow of oxygen when rotated counterclockwise and reduces resistance to the flow of oxygen when rotated clockwise. This can provide an intuitive user interface even though such a direction of rotation would be opposite conventional needle valves. In some implementations, the needle valve 1022 can be used in conjunction with the display 1020 to precisely control the oxygen fraction of the breathing gas output. In particular, in some implementations, the display 1020 shows the measured oxygen fraction of the output gas while the needle valve 1022 is being adjusted. This allows the user to adjust the oxygen fraction in real time based on feedback from the display 1020. A blower within the base unit 1002 may simultaneously be controlled to maintain a target flow rate while oxygen is being adjusted. For example, to maintain a constant flow rate, the blower may be accelerated when oxygen input is decreased and may be decelerated when the oxygen input is increased. Such a configuration allows a user to adjust oxygen fraction by adjusting a single variable, namely resistance to oxygen flow, without having to separately account for that variable's effects on another flow parameter, namely overall flow rate. This simplifies the adjustment of the oxygen fraction of breathing gas output from the base unit 1002 and eliminates the need for simultaneously, manually adjusting two variables using a look-up table.

The features of the liquid container 1050 facilitate its reversible connection to the base unit 1002. The liquid container 1050 includes the body 1052 and the cover 1054. The cover 1054 serves as a handle for rotating, lifting, and/or inserting the body 1052 of the liquid container 1050. The body 1052 is shaped to slide into the recess 1012 of the base unit 1002 and to be rotatable within the recess 1012. The body 1052 includes a plurality of breech lock tabs (not visible) extending radially outward which are disposed beneath the retention flanges 1030a-f. The breech lock tabs may press upward against the retention flanges 1030a-f when liquid is inside the liquid container 1050 if the liquid container 1050 has a flexible lower surface (e.g., as in system 200) and if the liquid within the liquid container 1050 is above ambient atmospheric pressure. Pressure exerted by the breech lock tabs against the retention flanges 1030a-f can increase friction against the retention flanges 1030a-f which increases the torque required to rotate the liquid container 1050 relative to the base unit 1002. This can prevent the liquid container 1050 from being inadvertently disconnected from the base unit 1002 when liquid is in the liquid container 1050.

The liquid line 1056 delivers liquid to the liquid container 1050 from a liquid source. In some implementations, the liquid line 1056 delivers liquid from a flexible bag suspended above the liquid container 1050. If the liquid source is sufficiently high above the liquid container 1050, the liquid line 1056 may deliver liquid at a pressure above ambient atmospheric pressure. The liquid line 1056 includes a clip 1057 which can be used to close the liquid line 1056 to prevent the communication of fluid between the liquid container 1050 and the liquid line 1056.

The delivery tube 1070 delivers gas from the base unit 1002 and liquid from the liquid container 1050 to a vapor transfer unit (not shown). The delivery tube 1070 includes the upstream portion 1070a and the downstream portion 1070b. The liquid delivery line 1072 and the liquid return line 1074 are disposed within the upstream portion 1070a and the downstream portion 1070b of the delivery tube 1070. The upstream portion 1070a of the delivery tube 1070, the liquid delivery line 1072, and the liquid return line 1074 connect to the liquid container 1050. The liquid delivery line 1072 receives liquid from the liquid container 1050 and directs the liquid toward the downstream portion 1070b of the delivery tube 1070 to the vapor transfer unit (not shown). The liquid return line 1074 receives liquid from the vapor transfer unit (not shown) and delivers the liquid to the liquid container 1050. Other than the liquid delivery line 1072 and the liquid return line 1074, the lumen of the upstream portion 1070a of the delivery tube 1070 is not in fluid communication with the downstream portion 107b of the delivery tube 1070. This is because the breathing gas is introduced into the delivery tube 1070 at the downstream connector 1008, but not at the upstream connector 1060. The downstream portion 1070b of the delivery tube 1070 is connected to the downstream connector 1008 of the delivery tube connector 1004. The downstream portion 1070b of the delivery tube 1070 directs breathing gas output from the downstream connector 1008 to the vapor transfer unit (not shown) via the downstream portion 1070b of the delivery tube 1070.

To further reduce the flow resistance of the respiratory therapy system 1000, the delivery tube 1070 has a relatively large inner diameter compared to conventional high flow therapy systems. In some implementations, the inner diameter of the delivery tube 1070 is more than about 5 mm. In certain implementations, the inner diameter of the delivery tube 1070 is about 15 mm. This larger diameter delivery tube 1070 further reduces the pressure required to operate the respiratory therapy system 1000.

The liquid delivery line 1072 and the liquid return line 1074 are disposed within the delivery tube 1070. Thus, the delivery tube 1070 insulates the liquid delivery line 1072 and the liquid return line 1074 from ambient air. The liquid in the liquid delivery line 1072 and the liquid return line 1074 is heated relative to the ambient air so that the liquid can be more easily converted to vapor at the vapor transfer unit. Maintaining the elevated temperature of the liquid in the liquid delivery line 1072 and the liquid return line 1074 requires a constant input of thermal energy, but the insulation provided by the delivery tube 1070 can reduce the required energy input compared to a system in which the fluid is exposed to ambient air. Furthermore, heat that is lost from the liquid delivery line 1072 and the liquid return line 1074 in the downstream portion 1070b of the delivery tube 1070 enters the flow of the breathing gas output of the base unit 1002. This warms the breathing gas output, which can facilitate the transfer of vapor into the breathing gas at the vapor transfer unit. Thus, some of the heat "lost" from the liquid delivery line 1072 and the liquid return line 1074 in the downstream portion 1070b is conserved within the breathing circuit.

Disposing the liquid delivery line 1072 and the liquid return line 1074 within the delivery tube 1070 also reduces the amount of tubing that must be managed by the user. In respiratory therapy systems in which a liquid container is separate from a breathing gas source, the user may have to manage two sets of tubes: tubes from the liquid container to the humidifier as well as tubes from the breathing gas source to the humidifier. In the system of the present disclosure, however, a single delivery tube 1070 provides both liquid and gas to a vapor transfer unit. This reduces the amount of space occupied by tubing and reduces the risk of snagging the tubing inadvertently.

Furthermore, disposing the liquid delivery line 1072 and the liquid return line 1074 within the delivery tube 1070 reduces the risk of kinking the liquid delivery line 1072, the liquid return line 1074, or the delivery tube 1070. This arrangement reduces the risk of kinking and occluding the delivery tube 1070 because the delivery tube 1070 shields the liquid lines 1072 and 1074 from kinking by increasing the minimum bend radius that the liquid lines 1072 and 1074 undergo during extreme bending. Moreover, in some implementations the delivery tube 1070 is corrugated to prevent or reduce kinking of the delivery tube 1070. Corrugation of the delivery tube 1070 can also prevent or reduce kinking of the liquid lines 1072 and 1074.

The delivery tube connector 1004 connects the delivery tube 1070 to the base unit 1002. The delivery tube connector includes the base 1010, the upstream connector 1006, the downstream connector 1008, and the wings 1009a-b. The upstream connector 1006 connects to the upstream portion 1070a of the delivery tube 1070, and the downstream connector 1008 connects to the downstream portion 1070b of the delivery tube 1070b. The upstream connector 1006 allows passage of the liquid lines 1072 and 1074 into the downstream connector 1008, but does not otherwise establish fluid communication between the downstream connector 1006 and the upstream connector 1008. The downstream connector 1008 establishes fluid communication between the breathing gas outlet (not shown) of the base unit 1002 and the downstream portion 1070b of the delivery tube 1070.

The delivery tube connector 1004 is reversibly coupled to the base unit 1002. The wings 1009a-b connect to the base unit 1002 by extending into a recess (not shown) on the side of the base unit 1002. The connection between the wings 1009a-b and the base unit 1002 is a snap fit. In certain implementations, the connection between the wings 1009a-b and the base unit 1002 is a friction fit, a twist or screw connection, a magnetic coupling, J-slot, other slotted connection, or any other suitable reversible coupling. The base 1010 of the delivery tube connector 1004 stabilizes the delivery tube connector 1004 against the base unit 1002. In some implementations, the wings 1009a-b and/or the base 1010 of the delivery tube connector 1004 include features to prevent rotation of the base 1010 of the delivery tube connector relative to the base unit 1002. In certain implementations, the connection between the delivery tube connector 1004 and the base unit 1002 is designed such that the delivery tube connector 1004 will disconnect from the base unit 1002 if the delivery tube 1070 is pulled suddenly. This can prevent a user from inadvertently toppling the entire base unit 1002 by accidentally yanking the delivery tube 1070.

By enabling easy connection and disconnection between the base unit 1002 and the liquid container 1050, the respiratory therapy system 1000 facilitates periodic replacement of the liquid container 1050 and associated liquid lines 1072 and 1074 to maintain sanitary operating conditions. At the same time, the connection between the base unit 1002 and the liquid container 1050 is secure enough to allow for stable operation of the system 1000 and to prevent inadvertent disconnection of the liquid container 1050. Additionally, the integration of the liquid container 1050 with the base unit 1020, along with the integration of the liquid lines 1072 and 1074 with the delivery tube 1070, simplifies the topology of the respiratory therapy system 1000. This facilitates management of tubing for the liquid and breathing gas paths, reduces the risk of kinking the liquid and breathing gas paths, and can conserve thermal energy of the liquid lines 1072 and 1074.

Figure 15:
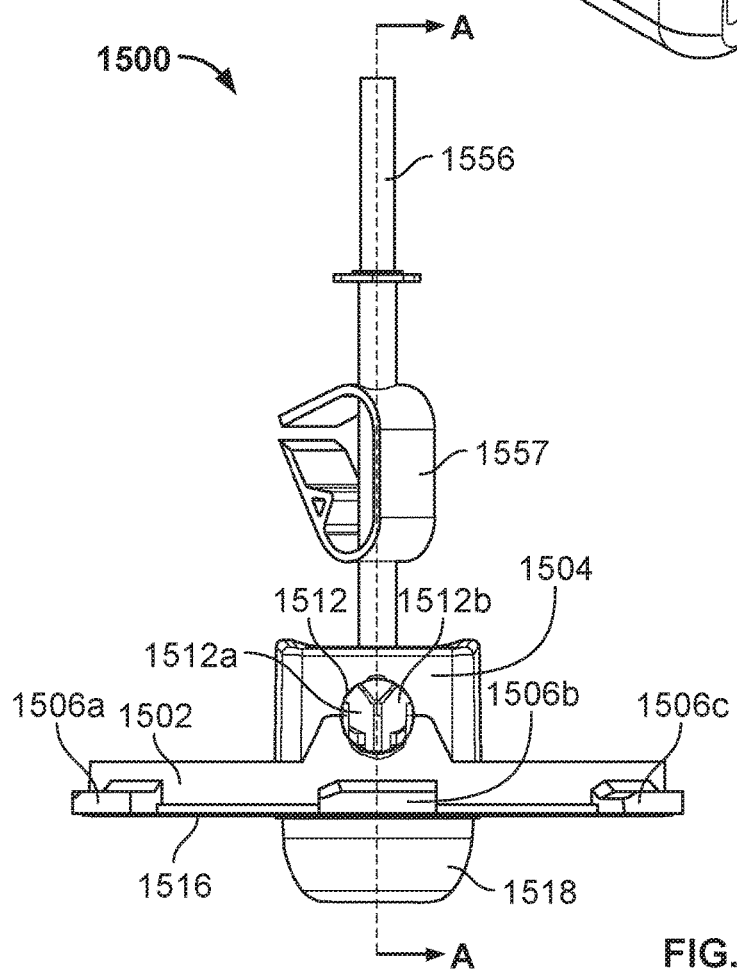
FIG. 15 shows a front view of an illustrative liquid container for a respiratory therapy system for high velocity nasal insufflation.
Figure 16:
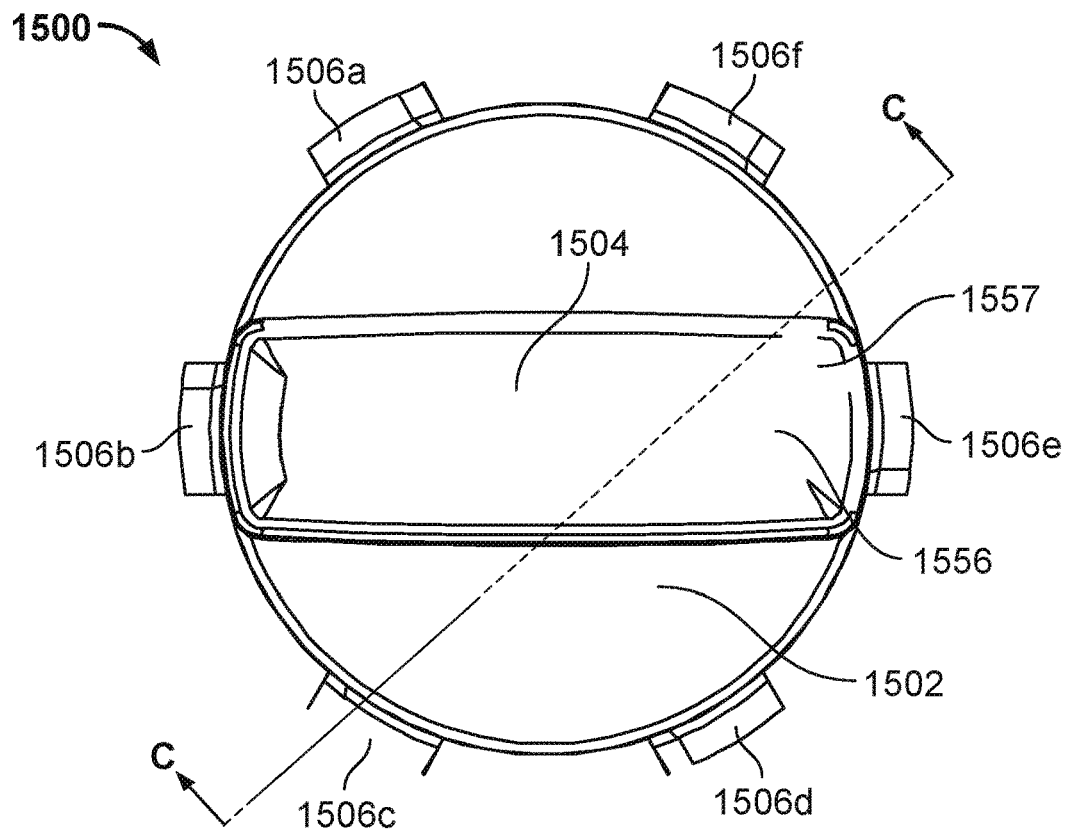
FIG. 16 shows a top view of the illustrative liquid container of FIG. 15.
Figure 17:
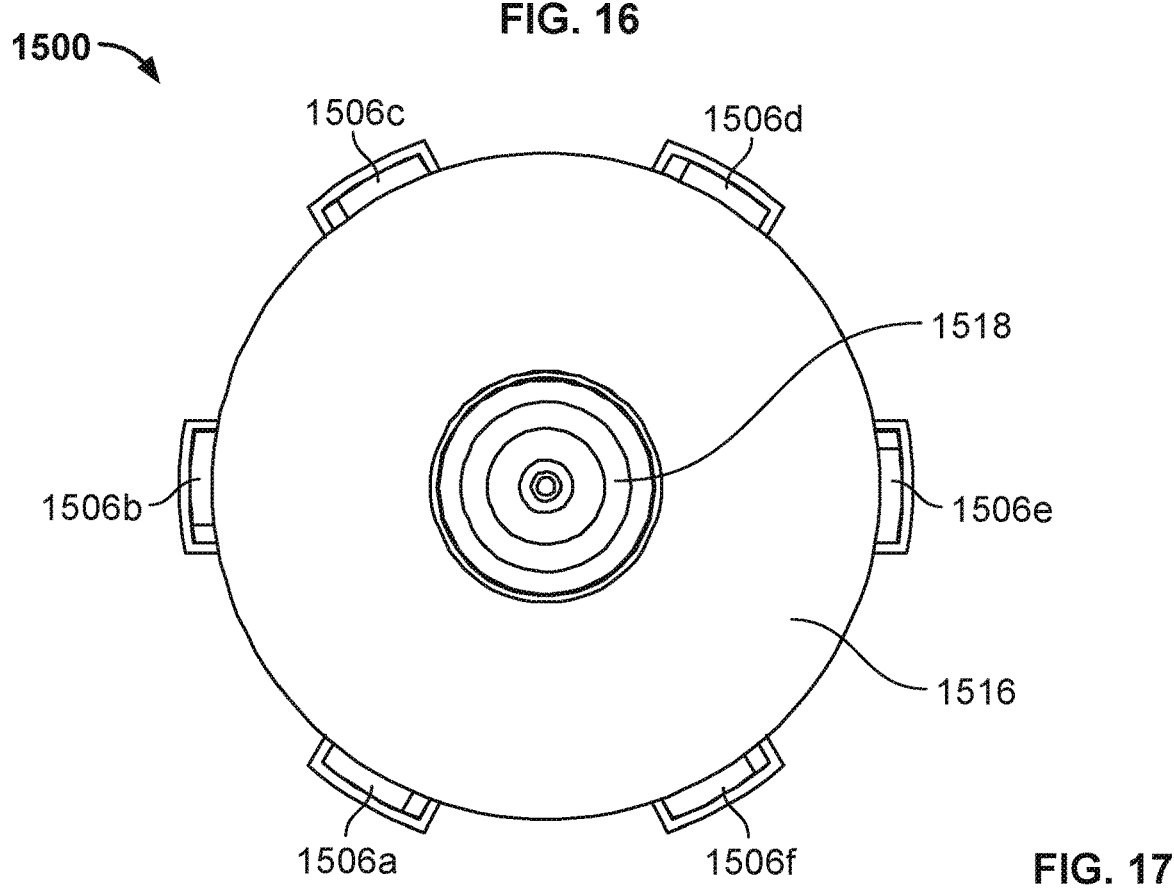
FIG. 17 shows a bottom view of the illustrative liquid container of FIGS. 15 and 16.
Figure 18:
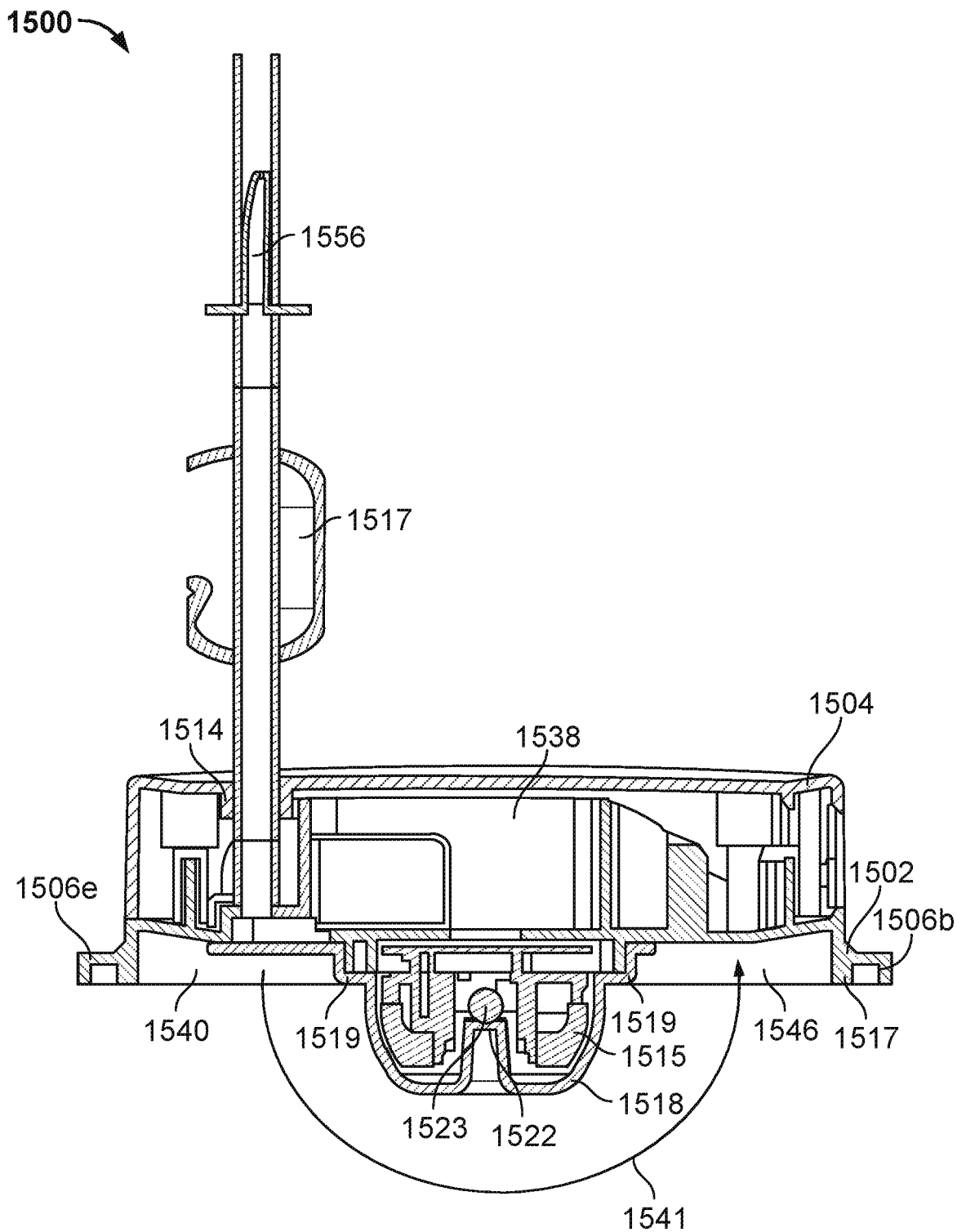
FIG. 18 shows a cross-sectional view of the illustrative liquid container of FIGS. 15-17 taken along section line A-A in FIG. 15.

FIGS. 15-18 show an illustrative liquid container 1500 for a respiratory therapy system for high velocity nasal insufflation according to some implementations. FIG. 15 shows a front view of the liquid container 1500, FIG. 16 shows a top view of the liquid container 1500, FIG. 17 shows a bottom view of the liquid container 1500, and FIG. 18 shows a cross-section of the liquid container 1500 taken along section line A-A in FIG. 15. The liquid container 300 may be used in the respiratory therapy system 100 of FIG. 1, the respiratory therapy system 200 of FIG. 2, or any other suitable respiratory therapy system. The liquid container 200 includes a body 1502, a cover 1504, a rotor cup 1518, a film 1516, a liquid line 1556, and a clip 1557. The body 1502 includes breech lock tabs 1505a-f, a tubing port 1512, an inlet 1514, a lower rim 1517, and cavities 1548, 1540, and 1546. The tubing port 1512 includes a delivery path 1512a and a return path 1512b The rotor cup 1518 includes a rotor 1515, rim 1519, a bearing 1523, and a bearing seat 1522.

The liquid container 1500 is depicted without tubing for clarity, but during use the liquid container 1500 includes two tubes: a first tube connected to the delivery path 1512a to direct liquid out of the liquid container 1500 and a second tube connected to the return path 1512b to direct liquid into the liquid container 1500.

The liquid container 1500 receives liquid from a liquid source, such as a water bag, and then heats and circulates the liquid. The liquid container 1500 initially receives liquid through the liquid line 1556 at the inlet 1514. The inlet 1514 is in fluid communication with the cavities 1538, 1540, and 1546. The cavities 1540 and 1546 are bounded on the upper part by the body 1502 and on the lower part by the film 1516. The film 1516 is joined in a fluid-tight manner to the lower rim 1517 of the body 1502 and the rim 1519 of the rotor cup 1518. Liquid in the cavities 1540 and 1546 may receive heat conducted across the film 1516 by an external heater (e.g., heater plates 220 and 222 of system 200). Liquid in the cavities 1540 and 1546 may be circulated in the direction indicated by the arrow 1541. This circulation is induced by the rotor 1515 disposed within the rotor cup 1518. In some implementations, the rotor 1515 is an impeller, such as a radially delivering impeller. In certain implementations, the rotor 1515 includes a magnet for being magnetically coupled to the base unit.

The cavities 1540 and 1546 are also in fluid communication with the return path 1512b and the delivery path 1512a (shown in FIG. 15). The return path 1512b receives liquid returning from the vapor transfer unit (not shown) and passes such liquid to the cavity 1538 like the liquid received via the inlet 1514. The circulated liquid is expelled through an outlet (not shown).

The liquid container 1500 is configured to mate with a base unit (e.g., the base unit 1002 of system 1000 of FIG. 10 above). To that end, the body 1502 includes the breech lock tabs 1505a-f. The breech lock tabs 1505a-f are disposed along the rim 1517 of the body 1502 and extend radially outward. The breech lock tabs 1505*a-f* allow the liquid container 1500 to be locked to a base unit with a twisting motion and unlocked by a similar twisting motion in the opposite direction. The breech lock design allows for simple and quick attachment to a base unit. Also, such an attachment mechanism is resistant to axial force, which may be developed by fluid pressure between the film 1516 and the base unit. Additionally, the breech lock design may make inadvertent disconnection of the liquid container 1500 more difficult during operation. This is because when liquid is in the cavities 1540 and 1546, the liquid exerts pressure against the film 1516, which in turn exerts pressure against the base unit (not shown), causing friction. Friction makes the breech lock more resistant to being twisted open. Thus, when fluid is in the container 1500 (i.e., during operation) the liquid container 1500 is more difficult to inadvertently disconnect from the base unit.

The rotor cup 1518 is dimensioned and configured to house a rotor for circulating liquid within the liquid container 1500. In some implementations, the rotor cavity 1520 of the rotor cup 1518 houses a magnet for magnetically coupling with the base unit. The magnet may rotate on a bearing seated on the bearing seat 1522. The bearing may be a spherical bearing, a hydrostatic bearing, a journal bearing, or any other suitable type of bearing.

By allowing liquid to be heated and circulated within the liquid container 1500, the liquid container can avoid exposing the components of the base unit to the liquid. This can permit the base unit to be reused with lower risk of contamination compared to liquid-contacting base units. Such a configuration makes disposal and replacement of the liquid container 1500 fairly simple.

Figure 19:
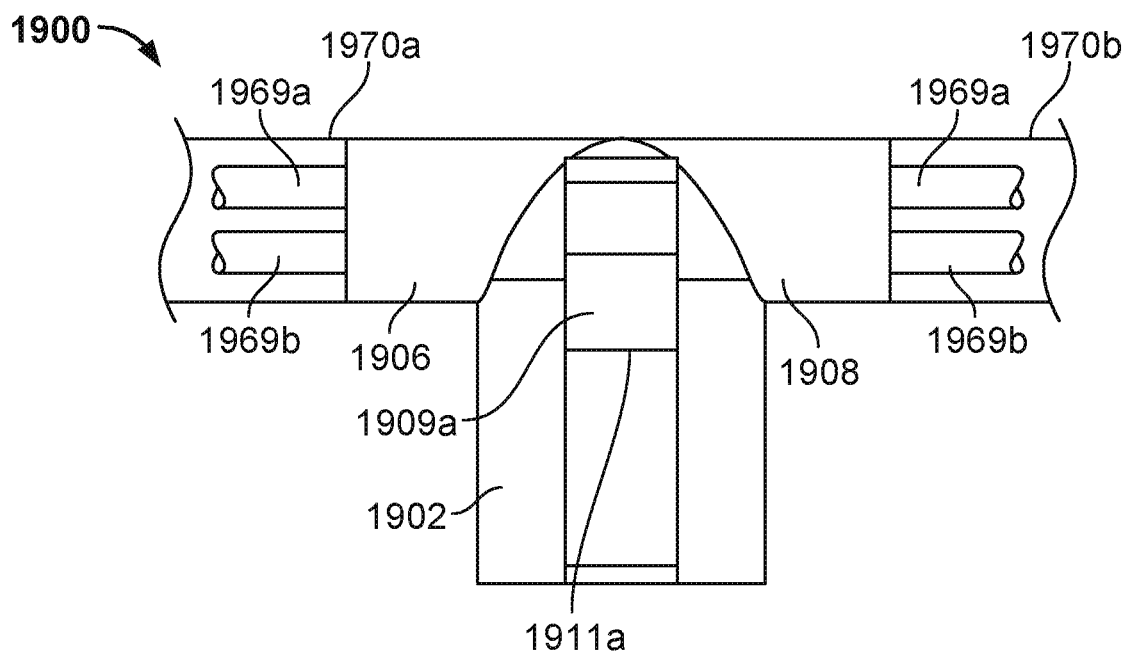
FIG. 19 shows a front view of an illustrative connector for managing the flow of gas and liquid through a respiratory therapy system.
Figure 20:
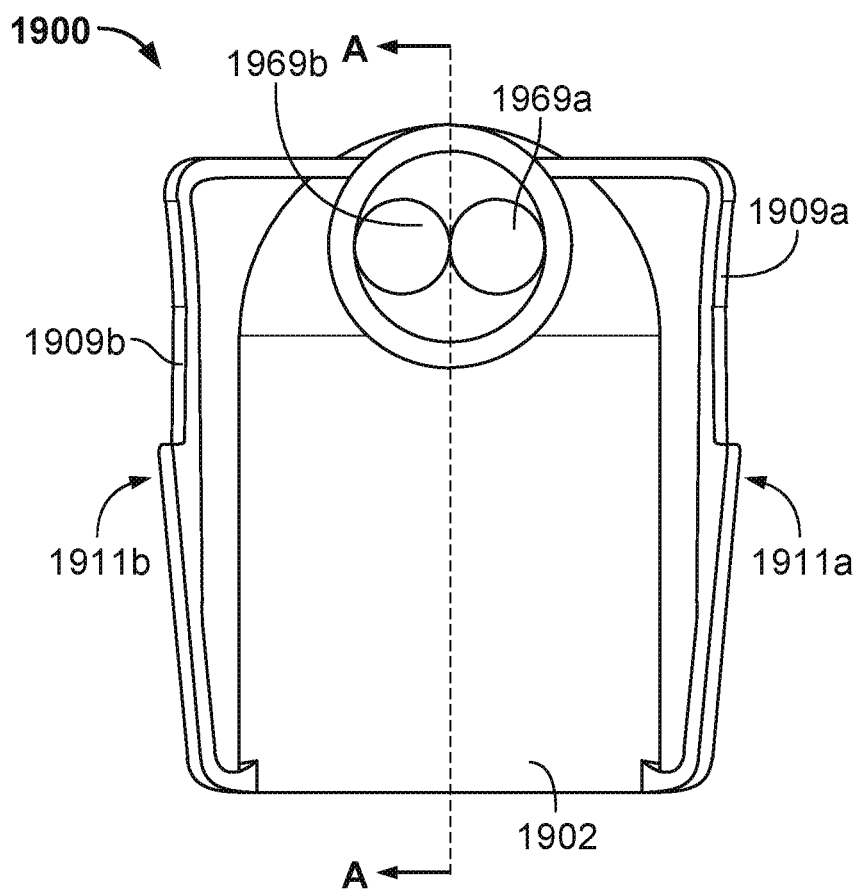
FIG. 20 shows a top view of the illustrative connector of FIG. 19.
Figure 21:
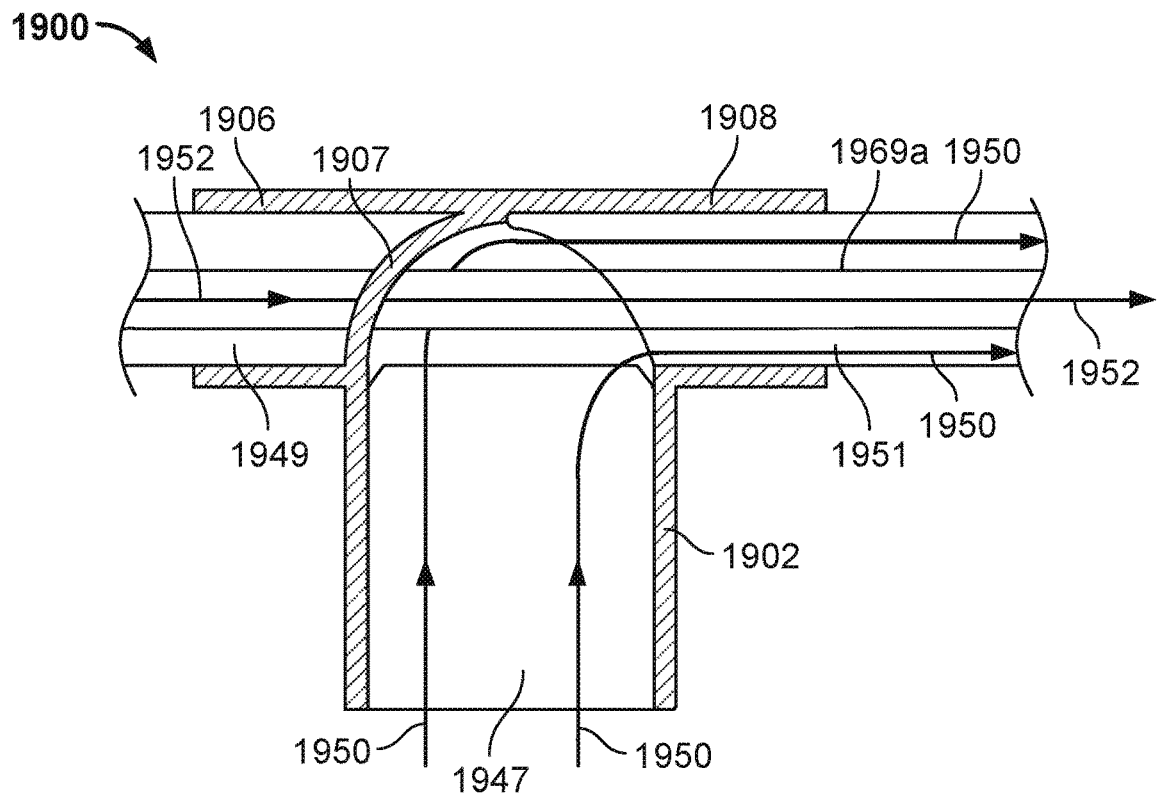
FIG. 21 shows a cross-sectional view of the illustrative connector of FIGS. 19 and 20 taken along section line A-A in FIG. 20.

FIGS. 19-21 show an illustrative connector 1900 for managing the flow of gas and liquid through a respiratory therapy system according to some implementations. FIG. 19 shows a front view of the connector 1900, FIG. 20 shows a top view of the connector 1900, and FIG. 21 shows a cross-section of the connector 1900 taken along section line A-A in FIG. 20. The connector 1900 is coupled to an upstream delivery tube portion 1970*a* and a downstream delivery tube portion 1970*b*. The connector 1900 includes a body 1902, an upstream connector 1906, a downstream connector 1908, wings 1909*a-b*, snap hooks 1911*a-b*, a breathing gas inlet 1947, an upstream lumen 1949, a breathing gas outlet 1951, and a barrier 1907. A liquid delivery line 1969*a* and a liquid return line 1969*b* pass through the connector 1900. The connector 1900 may be connected to a breathing gas outlet of a high flow therapy system. For example, the connector 1900 may be used in the system 1000 of FIG. 10 in place of the delivery tube connector 1004.

The connector 1900 receives breathing gas in the breathing gas inlet 1947 and directs the breathing gas toward the downstream delivery tube portion 1970*b* through the breathing gas outlet 1951 along the path indicated by arrows 1950. Thus, the inlet 1947 and outlet 1951 are in fluid communication. The lumen 1949 is not in communication with either inlet 1947 or outlet 1951 because the barrier 1907 prevents the breathing gas from travelling from the breathing gas inlet 1947 into the upstream lumen 1949. In some implementations, the breathing gas inlet 1947 is connected to a blower outlet or a base unit gas outlet. The downstream delivery tube portion 1970*b* connects to a vapor transfer unit (not shown) and the upstream delivery tube portion 1970*a* connects to a source of heated fluid (not shown).

The connector 1900 also allows passage of liquid lines 1969*a-b* from the upstream delivery tube portion 1970*a* to the downstream delivery tube portion 1970*b*. Thus, liquid can travel across the connector 1900 in the direction indicated by arrow 1952 (or in the opposite direction on return). The barrier 1907 includes two through holes to allow the passage of the liquid delivery line 1969*a* and the liquid return line 1969*b*. Since the upstream delivery tube portion 1970*a* and the downstream delivery tube portion 1970*b* surround the liquid delivery line 1969*a* and the liquid return line 1969*b*, the upstream delivery tube portion 1970*a* and the downstream delivery tube portion 1970*b* insulate the liquid delivery line 1969*a* and the liquid return line 1969*b* from ambient air. The liquid delivery line 1969*a* and the liquid return line 1969*b* carry heated liquid, so insulating the lines 1969*a* and 1969*b* can reduce the energy required to maintain the temperature of the lines 1969*a* and 1969*b* and thus reduce the energy requirements of the system in which connector 1900 is used. Moreover, heat that is lost from the liquid delivery line 1069*a* and the liquid return line 1069*b* in the downstream delivery tube portion 1970*b* enters the flow of the breathing gas output. This warms the breathing gas output, which can facilitate the transfer of vapor into the breathing gas at the vapor transfer unit (not shown). Thus, some of the heat "lost" from the liquid lines 1969*a-b* in the downstream delivery tube portion 1970*b* is conserved within the breathing circuit. Additionally, in some implementations, the blower delivers heated gas through the delivery tube. In such implementations, the heated gas heats the liquid in the liquid delivery line, thus reducing the power demand on a liquid heater.

Furthermore, by permitting the upstream delivery tube portion 1970*a* and the downstream delivery tube portion 1970*b* to surround the liquid delivery line 1969*a* and the liquid return line 1969*b*, the connector 1900 reduces the number of separate tubes that must be managed by the user. In respiratory therapy systems in which a liquid container is separate from a breathing gas source, the user may have to manage two sets of tubes: tubes from the liquid container to the humidifier as well as tubes from the breathing gas source to the humidifier. In a system employing the connector 1900, however, a gas path 1950 and two liquid lines 1969*a* and 1969*b* are all integrated within a single tube 1970*b*. This reduces the amount of space occupied by tubing and reduces the risk of snagging the tubing inadvertently.

Additionally, disposing the liquid delivery line 1969*a* and the liquid return line 1969*b* within the downstream delivery tube portion 1970*b* reduces the risk of kinking the liquid delivery line 1969*a*, the liquid return line 1969*b*, or the downstream delivery tube portion 1970*b*. This arrangement reduces the risk of kinking and occluding the downstream delivery tube portion 1970*b* because the downstream delivery tube portion 1970*b* shields the liquid lines 1969*a-b* from kinking by increasing the minimum bend radius that the liquid lines 1969*a-b* undergo during extreme bending. Moreover, in some implementations, the delivery tube portions 1970*a-b* are corrugated to prevent or reduce kinking of the delivery tube portions 1970*a-b*. Corrugation of the delivery tube portions 1970*a-b* can also prevent or reduce kinking of the liquid lines 1969*a-b*.

The connector 1900 is configured to reversibly couple to a base unit or blower. The wings 1909*a-b* are configured to connect to a base unit or blower using the snap hooks 1911*a-b*. In some implementations, the body 1902 is sized to fit within a bore or recess in a base unit or blower and the snap hooks 1911*a-b* are positioned to grab an internal edge of the bore or recess. In certain implementations, the connector 1900 is decoupled from such a recess by pressing inwardly on the wings 1909*a-b*. In certain implementations, the connection between the connector 1900 and the base unit is a friction fit, a twist or screw connection, a magnetic coupling, J-slot, other slotted connection, or any other suitable reversible coupling. In some implementations, the wings 1909a-b and/or the body 1902 of the connector 1900 include features to prevent the connector 1900 from rotating relative to the base unit. In certain implementations, the connection between the connector 1900 and the base unit is designed such that the connector 1900 will disconnect from the base unit if the either (or both) of the delivery tube portions 1970a-b is pulled suddenly. This can prevent a user from inadvertently toppling a base unit by accidently yanking the delivery tube portions 1970a-b.

Figure 22:
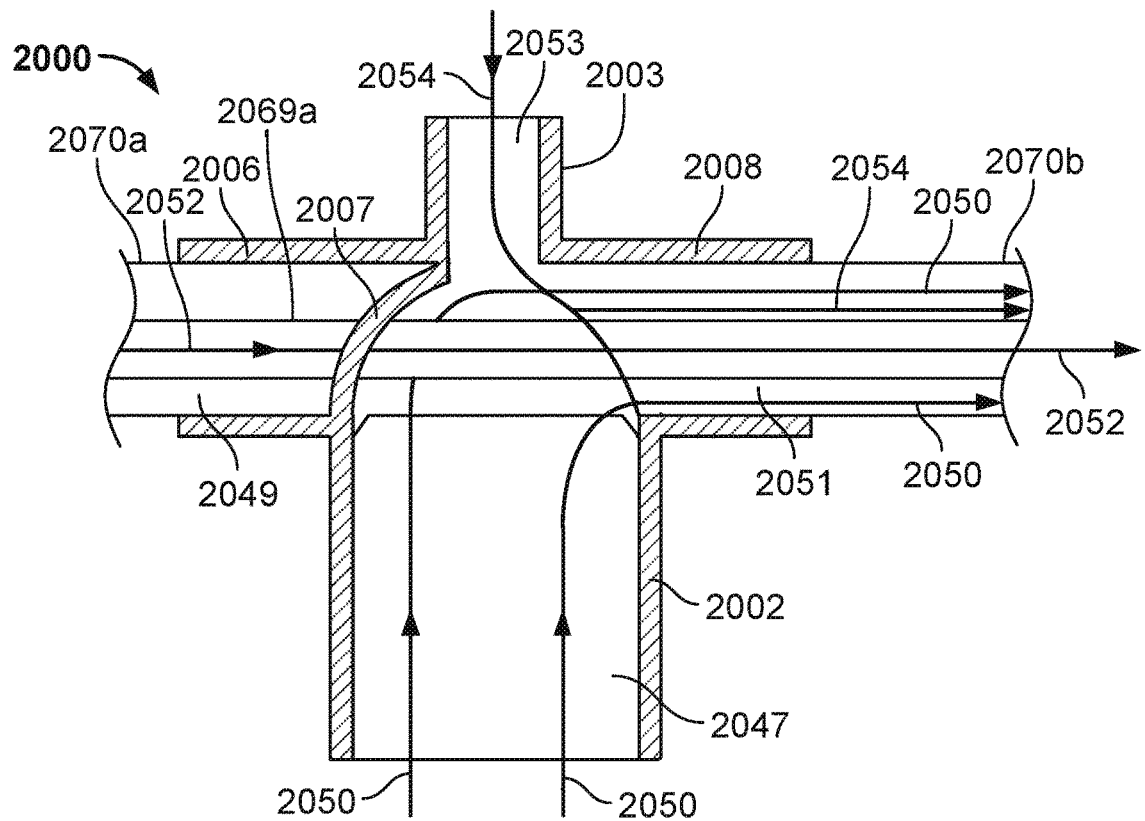
FIG. 22 shows a cross-sectional view of another embodiment of the illustrative connector of FIGS. 19-21.

While FIG. 21 shows a connector having one gas inlet 1947, FIG. 22 shows a cross-sectional view of an illustrative connector 2000 for having two gas inlets according to some implementations. The connector 2000 is coupled to an upstream delivery tube portion 2070a and a downstream delivery tube portion 2070b. The connector 2000 includes a body 2002, an upstream connector 2006, a downstream connector 2008, an auxiliary port 2003, wings 2009a-b, snap hooks 2011a-b, a breathing gas inlet 2047, an auxiliary inlet 2053, an upstream lumen 2049, a breathing gas outlet 2051, and a barrier 2007. A liquid delivery line 2069a and a liquid return line (not visible) pass through the connector 2000.

The auxiliary inlet 2003 is connected to a source of auxiliary gas, aerosol, or other fluid. In certain implementations, the auxiliary inlet 2003 receives nebulized medicament from a nebulizer. Such nebulized medicament can be pumped into the auxiliary inlet 2003 or may be drawn into the auxiliary inlet 2003 by means of a Venturi effect created by the flow of breathing gas along the path indicated by arrows 2050. Introducing medicament using the auxiliary inlet 2003 can simplify administration of medicament to the patient since medicament and breathing gas can be inhaled simultaneously from a common user interface. Also, since the auxiliary inlet 2003 is upstream from the humidifier, there is negligible risk of the auxiliary inlet 2003 causing excessive condensation compared to if the auxiliary inlet 2003 were downstream of a humidifier.

The connector 2000 receives breathing gas in the breathing gas inlet 2047 and directs the breathing gas toward the downstream delivery tube portion 2070b through the breathing gas outlet 2051 along the path indicated by arrows 2050. Thus, the inlet 2047 and outlet 2051 are in fluid communication. The lumen 2049 is not in communication with either inlet 2047 or outlet 2051 because the barrier 2007 prevents the breathing gas from travelling from the breathing gas inlet 2047 into the upstream lumen 2049. In some implementations, the breathing gas inlet 2047 of the connector 2000 is connected to a breathing gas outlet of a high flow therapy system. For example, the connector 2000 may be used in the system 1000 of FIG. 10 in place of the delivery tube connector 1004. The downstream delivery tube portion 2070b connects to a vapor transfer unit (not shown) and the upstream delivery tube portion 2070a connects to a source of heated fluid (not shown).

The connector 2000 also allows passage of liquid lines 2069a-b from the upstream delivery tube portion 2070a to the downstream delivery tube portion 2070b. Thus, liquid can travel across the connector 2000 in the direction indicated by arrow 2052 (or in the opposite direction on return). The barrier 2007 includes two through holes to allow the passage of the liquid delivery line 2069a and the liquid return line 2069b. Since the upstream delivery tube portion 2070a and the downstream delivery tube portion 2070b surround the liquid delivery line 2069a and the liquid return line 2069b, the upstream delivery tube portion 2070a and the downstream delivery tube portion 2070b insulate the liquid delivery line 2069a and the liquid return line 2069b from ambient air. The liquid delivery line 2069a and the liquid return line 2069b carry heated liquid, so insulating the lines 2069a and 2069b can reduce the energy required to maintain the temperature of the lines 2069a and 2069b and thus reduce the energy requirements of the system in which connector 2000 is reduced. Moreover, heat that is lost from the liquid delivery line 1069a and the liquid return line 1069b in the downstream delivery tube portion 2070b enters the flow of the breathing gas output. This warms the breathing gas output as well as the fluid introduced by the auxiliary inlet 2003, thereby facilitating the transfer of vapor into the gas at the vapor transfer unit (not shown). Thus, some of the heat "lost" from the liquid lines 2069a-b in the downstream delivery tube portion 2070b is conserved within the breathing circuit.

Furthermore, by permitting the upstream delivery tube portion 2070a and the downstream delivery tube portion 2070b to surround the liquid delivery line 2069a and the liquid return line 2069b, the connector 2000 reduces the number of separate tubes that must be managed by the user. In respiratory therapy systems in which a liquid container is separate from a breathing gas source, the user may have to manage two sets of tubes: tubes from the liquid container to the humidifier as well as tubes from the breathing gas source to the humidifier. In a system employing the connector 2000, however, a gas path 2050 and two liquid lines 2069a and 2069b are all integrated within a single tube 2070b. This reduces the amount of space occupied by tubing and reduces the risk of snagging the tubing inadvertently.

Additionally, disposing the liquid delivery line 2069a and the liquid return line 2069b within the downstream delivery tube portion 2070b reduces the risk of kinking the liquid delivery line 2069a, the liquid return line 2069b, or the downstream delivery tube portion 2070b. This arrangement reduces the risk of kinking and occluding the downstream delivery tube portion 2070b because the downstream delivery tube portion 2070b shields the liquid lines 2069a-b from kinking by increasing the minimum bend radius that the liquid lines 2069a-b undergo during extreme bending. Moreover, in some implementations, the delivery tube portions 2070a-b are corrugated to prevent or reduce kinking of the delivery tube portions 2070a-b. Corrugation of the delivery tube portions 2070a-b can also prevent or reduce kinking of the liquid lines 2069a-b.

The connector 2000 is configured to reversibly couple to a base unit or blower. The wings 2009a-b are configured to connect to a base unit or blower using the snap hooks 2011a-b. In some implementations, the body 2002 is sized to fit within a bore or recess in a base unit or blower and the snap hooks 2011a-b are positioned to grab an internal edge of the bore or recess. In certain implementations, the connector 2000 is decoupled from such a recess by pressing inwardly on the wings 2009a-b. In certain implementations, the connection between the connector 2000 and the base unit is a friction fit, a twist or screw connection, a magnetic coupling, J-slot, other slotted connection, or any other suitable reversible coupling. In some implementations, the wings 2009a-b and/or the body 2002 of the connector 2000 include features to prevent the connector 2000 from rotating relative to the base unit. In certain implementations, the connection between the connector 2000 and the base unit is designed such that the connector 2000 will disconnect from the base unit if the either (or both) of the delivery tube portions 2070a-b is pulled suddenly. This can prevent a user from inadvertently toppling a base unit by accidently yanking the delivery tube portions 2070*a-b*.

By introducing medicament using the auxiliary inlet 2003, the connector 2000 can simplify administration of medicament to the patient. Since medicament and breathing gas can be inhaled simultaneously from a common user interface, a patient may enjoy increased comfort which may lead to increased compliance. Also, since the auxiliary inlet 2003 is upstream from the humidifier, there is negligible risk of the auxiliary inlet 2003 causing excessive condensation compared to if the auxiliary inlet 2003 were downstream of a humidifier.

Figure 23:
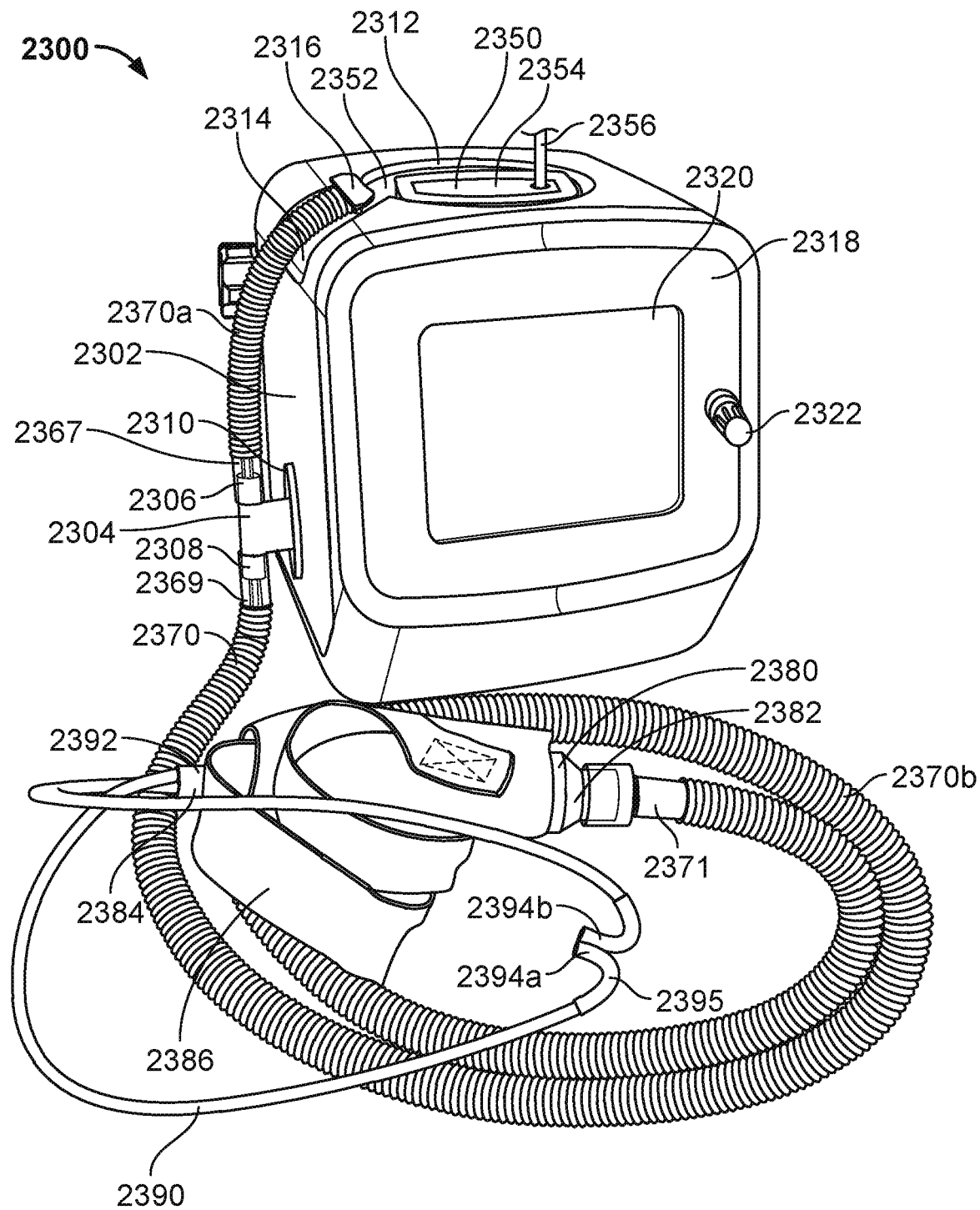
FIG. 23 shows a perspective view of an illustrative respiratory therapy system for high velocity nasal insufflation.

FIG. 23 shows a perspective view of an illustrative respiratory therapy system 2300 for high velocity nasal insufflation according to some implementations. The respiratory therapy system 2300 includes a base unit 2302, a liquid container 2350, a liquid line 2356, a delivery tube 2370, a delivery tube connector 2304, a vapor transfer unit 2380, and a nasal cannula 2390. The base unit 2302 includes a recess 2312, a recess 2314, a retention tab 2316, a front panel 2318, a display 2320, a needle valve knob 2322, a pole mount (not visible), and feet (not visible). The liquid container 2350 includes a body 2352, and a cover 2354. The delivery tube 2370 includes an upstream tube portion 2370*a*, a downstream tube portion 2370*b*, a liquid delivery line (not visible), and a liquid return line (not visible). The delivery tube connector 2304 includes a base 2310, an upstream connector 2306, a downstream connector 2308, and wings (not visible).

The base unit 2302 is reversibly coupled to the liquid container 2350. The recess 2312 of the base unit 2302 accepts the body 2352 of the liquid container 2350. The recess 2314 of the base unit accepts the upstream portion 2370*a* of the delivery tube 2370 so that the delivery tube 2370 can connect to the liquid container 2350 while the liquid container 2350 is within the recess 2312. The retention tab 2316 mates with the upstream portion 2370*a* of the delivery tube 2370 to retain the delivery tube 2370 within the recess 2314. The retention tab 2316 does not extend across the entire recess 2314 so that the delivery tube 2370 can be removed from the recess 2314 by rotating and lifting the liquid container 2350 relative to the base unit 2302. In the implementation of FIG. 23, such removal can be achieved by rotating the liquid container 2350 counter clockwise. In some implementations, the recess 2314 includes retention flanges which mate with breech lock tabs on the liquid container 2350 to retain the liquid container 2350 within the recess 2314. Any suitable number of retention flanges may be used (e.g., 1, 2, 3, 4, 5, 6, 7, 8, >8 or any other suitable number). In some implementations, the liquid container 2350 is coupled to the base unit without the use of a breech lock configuration. For example, in certain implementations, the liquid container 2350 slides linearly into the base unit 2302 to interlock with the base unit. In certain implementations, the liquid container 2350 couples to the base unit 2302 by a friction fit, an interference fit, a snap fit, a mechanical fastener, a magnetic coupling, or any other suitable coupling.

The base unit 2302 receives air and/or oxygen and outputs pressurized gas. The base unit 2302 receives air through an air inlet and can receive oxygen through an oxygen inlet. The base unit 2302 includes a blower (not visible), which pressurizes the air and/or oxygen within the base unit 2302. The air inlet can receive ambient air at atmospheric pressure. The oxygen inlet can accept oxygen at atmospheric pressure or at a higher pressure. The oxygen inlet can accept oxygen from an oxygen concentrator.

The base unit 2302 allows the output of breathing gas to be controlled by a user via features of the front panel 2318. The front panel 2318 is angled slightly upward. This allows a user to read and operate the front panel 2318 even when the base unit 2302 is positioned at a relatively low height (e.g., on a bedside night stand) or at a relatively high height (e.g., on an IV pole). The base unit 2302 can be supported by feet (not shown) when sitting on a horizontal surface, such as a night stand or other table. The base unit 2302 can be supported by a pole mount (not shown) when mounted on an IV pole or any other pole.

The front panel 2318 includes the display 2320 and the needle valve 2322. In some implementations, the display 2320 is a touchscreen user interface. In certain implementations, the display 2320 presents the flow rate of breathing gas output, the oxygen fraction of breathing gas output, the temperature of breathing gas output, the flow rate set point, the oxygen fraction set point, the temperature set point, overheating warnings, flow occlusion warnings, low flow resistance warnings, liquid depletion warnings, and/or any other suitable information relevant to respiratory therapy.

The needle valve 2322 controls the amount of oxygen accepted by the base unit 2302. In some implementations, the needle valve 2322 restricts the flow of oxygen when rotated counterclockwise and reduces resistance to the flow of oxygen when rotated clockwise. This can provide an intuitive user interface even though such a direction of rotation would be opposite conventional needle valves. In some implementations, the needle valve 2322 is used in conjunction with the display 2320 to precisely control the oxygen fraction of the breathing gas output. In particular, in some implementations, the display 2320 shows the measured oxygen fraction of the output gas while the needle valve 2322 is being adjusted. This allows the user to adjust the oxygen fraction in real time based on feedback from the display 2320. A blower within the base unit 2302 may simultaneously be controlled to maintain a target flow rate while oxygen is being adjusted. For example, to maintain a constant flow rate, the blower may be accelerated when oxygen input is decreased and may be decelerated when the oxygen input is increased. Such a configuration allows a user to adjust oxygen fraction by adjusting a single variable, namely resistance to oxygen flow, without having to separately account for that variable's effects on another flow parameter, namely overall flow rate. This simplifies the adjustment of the oxygen fraction of breathing gas output from the base unit 2302 and eliminates the need for simultaneously, manually adjusting two variables using a look-up table.

The features of the liquid container 2350 facilitate its reversible connection to the base unit 2302. The liquid container 2350 includes the body 2352 and the cover 2354. The cover 2354 serves as a handle for rotating, lifting, and/or inserting the body 2352 of the liquid container 2350. The body 2352 is shaped to slide into the recess 2312 of the base unit 2302 and to be rotatable within the recess 2312. The body 2352 may include a plurality of breech lock tabs extending radially outward which are disposed beneath the retention flanges. The breech lock tabs may press upward against retention flanges when liquid is inside the liquid container 2350 if the liquid container 2350 has a flexible lower surface (e.g., as in system 200) and if the liquid within the liquid container 2350 is above ambient atmospheric pressure. Pressure exerted by the breech lock tabs against the retention flanges can increase friction against the retention flanges which increases the torque required to rotate the liquid container 2350 relative to the base unit 2302. This can prevent the liquid container 2350 from being inadvertently disconnected from the base unit 2302 when liquid is in the liquid container 2350.

The liquid line 2356 delivers liquid to the liquid container 2350 from a liquid source. In some implementations, the liquid line 2356 delivers liquid from a flexible bag suspended above the liquid container 2350. If the liquid source is sufficiently high above the liquid container 2350, the liquid line 2356 may deliver liquid at a pressure above ambient atmospheric pressure. The liquid line 2356 may include a clip which can be used to close the liquid line 2356 to prevent the communication of fluid between the liquid container 2350 and the liquid line 2356.

The delivery tube 2370 delivers gas from the base unit 2302 and liquid from the liquid container 2350 to the vapor transfer unit 2380. The delivery tube 2370 includes the upstream portion 2370*a* and the downstream portion 2370*b*. The liquid delivery line (not visible) and the liquid return line (not visible) are disposed within the upstream portion 2370*a* and the downstream portion 2370*b* of the delivery tube 2370. The upstream portion 2370*a* of the delivery tube 2370, the liquid delivery line, and the liquid return line connect to the liquid container 2350. The liquid delivery line receives liquid from the liquid container 2350 and directs the liquid toward the downstream portion 2370*b* of the delivery tube 2370 to the vapor transfer unit 2380. The liquid return line receives liquid from the vapor transfer unit 2380 and delivers the liquid to the liquid container 2350. Other than the liquid delivery line and the liquid return line, the lumen of the upstream portion 2370*a* of the delivery tube 2370 is not in fluid communication with the downstream portion 237*b* of the delivery tube 2370. This is because the breathing gas is introduced into the delivery tube 2370 at the downstream connector 2308, but not at the upstream connector 2360. The downstream portion 2370*b* of the delivery tube 2370 is connected to the downstream connector 2308 of the delivery tube connector 2304. The downstream portion 2370*b* of the delivery tube 2370 directs breathing gas output from the downstream connector 2308 to the vapor transfer unit 2380 via the downstream portion 2370*b* of the delivery tube 2370.

To further reduce the flow resistance of the respiratory therapy system 2300, the delivery tube 2370 has a relatively large inner diameter compared to conventional high flow therapy systems. In some implementations, the inner diameter of the delivery tube 2370 is more than about 5 mm. In certain implementations, the inner diameter of the delivery tube 2370 is about 15 mm. This larger diameter delivery tube 2370 further reduces the pressure required to operate the respiratory therapy system 2300.

The liquid delivery line and the liquid return line are disposed within the delivery tube 2370. Therefore, the delivery tube 2370 insulates the liquid delivery line and the liquid return line from ambient air. The liquid in the liquid delivery line and the liquid return line is heated relative to the ambient air so that the liquid can be more easily converted to vapor at the vapor transfer unit 2380. Maintaining the elevated temperature of the liquid in the liquid delivery line and the liquid return line requires a constant input of thermal energy, but the insulation provided by the delivery tube 2370 can reduce the required energy input compared to a system in which the fluid is exposed to ambient air. Furthermore, heat that is lost from the liquid delivery line and the liquid return line in the downstream portion 2370*b* of the delivery tube 2370 enters the flow of the breathing gas output of the base unit 2302. This warms the breathing gas output, which can facilitate the transfer of vapor into the breathing gas at the vapor transfer unit 2380. Thus, some of the heat "lost" from the liquid delivery line and the liquid return line in the downstream portion 2370*b* is conserved within the breathing circuit.

Disposing the liquid delivery line and the liquid return line within the delivery tube 2370 also reduces the amount of tubing that must be managed by the user. In respiratory therapy systems in which a liquid container is separate from a breathing gas source, the user may have to manage two sets of tubes: tubes from the liquid container to the humidifier as well as tubes from the breathing gas source to the humidifier. In the system of the present disclosure, however, a single delivery tube 2370 provides both liquid and gas to the vapor transfer unit 2380. This reduces the amount of space occupied by tubing and reduces the risk of snagging the tubing inadvertently.

Furthermore, disposing the liquid delivery line and the liquid return line within the delivery tube 2370 reduces the risk of kinking the liquid delivery line, the liquid return line, or the delivery tube 2370. This arrangement reduces the risk of kinking and occluding the delivery tube 2370 because the delivery tube 2370 shields the liquid lines from kinking by increasing the minimum bend radius that the liquid lines undergo during extreme bending. Moreover, the delivery tube 2370 is corrugated to prevent or reduce kinking of the delivery tube 2370. Corrugation of the delivery tube 2370 can also prevent or reduce kinking of the liquid lines.

The delivery tube connector 2304 connects the delivery tube 2370 to the base unit 2302. The delivery tube connector includes the base 2310, the upstream connector 2306, the downstream connector 2308, and the wings. The upstream connector 2306 connects to the upstream portion 2370*a* of the delivery tube 2370, and the downstream connector 2308 connects to the downstream portion 2370*b* of the delivery tube 2370*b*. The upstream connector 2306 allows passage of the liquid lines into the downstream connector 2308, but does not otherwise establish fluid communication between the downstream connector 2306 and the upstream connector 2308. The downstream connector 2308 establishes fluid communication between the breathing gas outlet of the base unit 2302 and the downstream portion 2370*b* of the delivery tube 2370.

The delivery tube connector 2304 is reversibly coupled to the base unit 2302. The connector 2304 connects to the base unit 2302 by extending into a recess (not shown) on the side of the base unit 2302. In some implementations, the connection between the connector 2304 and the base unit 2302 is a snap fit. In certain implementations, the connection between the connector 2304 and the base unit 2302 is a friction fit, a twist or screw connection, a magnetic coupling, J-slot, other slotted connection, or any other suitable reversible coupling. The base 2310 of the delivery tube connector 2304 stabilizes the delivery tube connector 2304 against the base unit 2302. In some implementations, the delivery tube connector 2304 includes features to prevent rotation of the base 2310 of the delivery tube connector relative to the base unit 2302. In certain implementations, the connection between the delivery tube connector 2304 and the base unit 2302 is designed such that the delivery tube connector 2304 will disconnect from the base unit 2302 if the delivery tube 2370 is pulled suddenly. This can prevent a user from inadvertently toppling the entire base unit 2302 by accidently yanking the delivery tube 2370.

By enabling easy connection and disconnection between the base unit 2302 and the liquid container 2350, the respiratory therapy system 2300 facilitates periodic replacement of the liquid container 2350 and associated liquid lines to maintain sanitary operating conditions. At the same time, the connection between the base unit 2302 and the liquid container 2350 is secure enough to allow for stable operation of the system 2300 and to prevent inadvertent disconnection of the liquid container 2350. Additionally, the integration of the liquid container 2350 with the base unit 2320, along with the integration of the liquid lines with the delivery tube 2370, simplifies the topology of the respiratory therapy system 2300. This facilitates management of tubing for the liquid and breathing gas paths, reduces the risk of kinking the liquid and breathing gas paths, and can conserve thermal energy of the liquid lines.

The vapor transfer unit 2380 receives gas from the base unit 2302 and liquid from the liquid container 2350 and delivers humidified gas through the gas outlet 118 to the nasal cannula 122. Gas received by the vapor transfer unit 2380 travels through a gas passage (not visible) before exiting the gas outlet 2384. In the gas passage, the gas is humidified by vapor. In some implementations, the vapor transfer unit 2380 includes a membrane that permits diffusion of liquid through the membrane from the liquid passage (not visible) to the gas passage, where the liquid becomes a vapor and is incorporated into the gas flow. Simultaneously, liquid may circulate within the liquid passage. The remainder of the liquid may return to the liquid container 2350 through the return liquid line within the delivery tube 2370. The gas passage within the vapor transfer unit 2380 provides a relatively low flow resistance. For example, at a flow rate of 40 LPM, the flow resistance of the vapor transfer unit 2380 may be <70 kPa, <60 kPa, <50 kPa, <40 kPa, <30 kPa, <25 kPa, <20 kPa, <15 kPa, <10 kPa, <5 kPa, <4 kPa, <3 kPa, <2 kPa, <1 kPa, or any other suitable flow resistance. The low flow resistance of the vapor transfer unit 2380 helps enable the low pressure operation of the system 2300, which in turn enables the system to driven by a blower rather than a high pressure source.

The vapor transfer membrane may be a non-porous membrane that allows the passage of water vapor. In some implementations, the membrane is Pebax or any other suitable polymer. In some implementations, the vapor transfer unit includes several vapor transfer membranes. For example, the vapor transfer unit may include a plurality of vapor transfer tubes or pleated sheets. Further vapor transfer membrane designs compatible with the present disclosure are described in U.S. patent application Ser. Nos. 14/675,198 and 14/983,225, the contents of which are hereby incorporated by reference in their entirety.

The vapor transfer unit 2380 is configured to be positioned proximate to the patient (e.g., within 10 feet, 6 feet, 3 feet, 2 feet, 1 foot, or 6 inches or the patient's airway), so as to reduce the length of tubing through which the humidified air has to travel to reach the patient. Since the diameter of tubing carrying heated and humidified gas must be relatively small to prevent condensation (e.g., 5 mm ID), reducing the length that the heated and humidified gas must travel reduces the length of the small diameter tubing. This reduces the resistance to air flow through the system, thereby enabling the system to operate at a lower pressure.

The nasal cannula 2390 receives humidified breathing gas from the gas outlet 2370 of the vapor transfer unit 2380 and outputs the humidified breathing gas through the nasal prongs 2394a and 2394b. The nasal prongs 2394a-b have a relatively small internal diameter to ensure a relatively high exit velocity of the breathing gas. In some implementations, the internal diameter of the nasal prongs 2394a-b is <6 mm, <5 mm, <4 mm, <3 mm, <2 mm, or any other suitable diameter. A high exit velocity allows the breathing gas to better flush carbon dioxide from a patient's airways.

The nasal cannula 2390 is configured to have a low flow resistance. For example, the nasal prong 2394a and the nasal prong 2394b each have separate gas flow paths which do not collide at the nasal cannula body 2395. Furthermore, in some implementations, the nasal cannula 2390 has a relatively short length to lower the flow resistance of the nasal cannula 2390. In certain implementations, the nasal cannula 2390 has a length of <2.5 m, <2 m, <1.5 m, <1 m, <0.5 m, or any other suitable length. Nasal cannula designs compatible with the present disclosure are disclosed in U.S. patent application Ser. No. 13/665,100 and U.S. Provisional Patent Application No. 62/555,945, the contents of which are hereby incorporated by reference in their entirety.

By using a low resistance vapor transfer unit 2380, nasal cannula 2390, and delivery tube 2370, the respiratory therapy system 2300 enables delivery of high velocity, humidified breathing gas with a relatively low pressure source, such as a blower. The use of a low pressure source enables the use of the system 2300 in a variety of environments in which high pressure sources are not available (e.g., at home, in an ambulance, in an outpatient care facility).

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in high flow therapy and mechanical ventilation systems, may be applied to systems, devices, and methods to be used in other ventilation circuits.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A system for delivering breathing gas, the system comprising:
   a base unit configured for mobile use in a patient care environment comprising:
      a blower;
      a heating element for heating liquid, the heating element having a heating surface; and
      a force sensor;
   a vapor transfer unit external to the base unit and comprising:
      a gas passage,
      a liquid passage,
      a gas outlet, and
      a membrane separating the gas passage and the liquid passage, wherein the membrane permits transfer of vapor into the gas passage from liquid in the liquid passage; a nasal cannula coupled to the gas outlet; and
   a liquid container configured to reversibly mate with the base unit, the liquid container having a surface formed of an elastic flexible film, wherein the elastic flexible film is configured to mate with and to conform to the heating surface when the liquid container mates with the base unit, wherein the force sensor is configured to measure the force applied by a deformation of the elastic flexible film onto the force sensor to determine a pressure of the liquid in the liquid container to determine an amount of liquid in the liquid container when the liquid container is coupled to the base unit.

2. The system of claim 1, wherein the liquid container interlocks with a surface of the base unit.

3. The system of claim 1, wherein the blower is configured to pressurize breathing gas to less than about 276 kPa (40 psi).

4. The system of claim 1, wherein the liquid container includes an impeller.

5. The system of claim 4, wherein the base unit includes a motor.

6. The system of claim 5, wherein the motor is magnetically coupled to the impeller.

7. The system of claim 1, wherein the liquid passage is coupled to the liquid container by a first tube.

8. The system of claim 7, wherein the gas passage is coupled to the blower by a second tube.

9. The system of claim 8, wherein the first tube passes within the second tube.

10. The system of claim 8, wherein the second tube has an inner diameter of more than about 5 mm.

11. The system of claim 1, wherein the membrane is non-porous.

12. The system of claim 1, wherein the nasal cannula includes an outlet having a cross sectional area less than a cross sectional area of a patient's nostril.

13. The system of claim 1, wherein the base unit further comprises an oxygen sensor.

14. The system of claim 1, further comprising an oxygen source.

15. The system of claim 1, further comprising an oxygen concentrator.

16. The system of claim 14 wherein the oxygen source includes an oxygen outlet, wherein the blower includes a blower inlet, the oxygen outlet being coupled to the blower inlet.

17. The system of claim 16, wherein the oxygen outlet is coupled to the blower inlet by a needle valve.

18. The system of claim 1, wherein the blower includes a blower outlet and wherein the liquid container includes a liquid inlet and a liquid outlet, and wherein the liquid inlet and the liquid outlet are each spaced from the blower outlet by at least 10 cm.

19. The system of claim 1, wherein the flexible film is positioned against the force sensor when the liquid container mates with the base unit.

20. The system of claim 1, further comprising a controller configured to receive information from the force sensor, wherein the information includes the pressure of the liquid in the liquid container indicating a level of the liquid in the liquid container.

21. The system of claim 20, wherein the controller is configured to, based on the received information, shut off the system.

22. The system of claim 20, wherein the controller is configured to, based on the received information, provide a warning to a user that the liquid container needs to be replenished.

* * * * *